United States Patent
Watowich et al.

(10) Patent No.: US 12,071,409 B2
(45) Date of Patent: *Aug. 27, 2024

(54) QUINOLINE DERIVED SMALL MOLECULE INHIBITORS OF NICOTINAMIDE N-METHYLTRANSFERASE (NNMT) AND USES THEREOF

(71) Applicant: The Board of Regents of the University of Texas System, Austin, TX (US)

(72) Inventors: Stanley Watowich, Galveston, TX (US); Harshini Neelakantan, Galveston, TX (US); Hua-Yu Wang, Galveston, TX (US); Stanton Mchardy, Galveston, TX (US)

(73) Assignee: The Board of Regents of the University of Texas, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/834,847

(22) Filed: Jun. 7, 2022

(65) Prior Publication Data

US 2023/0107256 A1   Apr. 6, 2023

Related U.S. Application Data

(63) Continuation of application No. 16/499,228, filed as application No. PCT/US2018/025134 on Mar. 29, 2018, now Pat. No. 11,401,243.

(60) Provisional application No. 62/559,417, filed on Sep. 15, 2017, provisional application No. 62/479,256, filed on Mar. 30, 2017.

(51) Int. Cl.
*C07D 215/42* (2006.01)
*C07D 215/10* (2006.01)
*C07D 215/26* (2006.01)
*C07D 405/06* (2006.01)

(52) U.S. Cl.
CPC ......... *C07D 215/42* (2013.01); *C07D 215/10* (2013.01); *C07D 215/26* (2013.01); *C07D 405/06* (2013.01)

(58) Field of Classification Search
CPC .. C07D 215/42; C07D 215/10; C07D 215/26; C07D 405/06
See application file for complete search history.

(56) References Cited

U.S. PATENT DOCUMENTS

| | | | | |
|---|---|---|---|---|
| 3,556,800 A * | 1/1971 | Kimura | ............... | G03C 1/29 430/584 |
| 5,817,520 A * | 10/1998 | Yadan | ............... | G01N 33/6815 546/180 |
| 11,401,243 B2 * | 8/2022 | Watowich | ............... | C07D 401/06 |
| 2003/0196281 A1 * | 10/2003 | Sauter | ............... | A61K 8/347 8/405 |

OTHER PUBLICATIONS

Lorz; J. Am. Chem. Soc. 1951, 73, 1, 483-485. https://doi.org/10.1021/ja01145a525 (Year: 1951).*
Rusinov; Russian Journal of Organic Chemistry (Translation of Zhurnal Organicheskoi Khimii), 1998, 34, 263-270. (Year: 1998).*
Horning; J. Am. Chem. Soc. 2016, 138, 40, 13335-13343. https://doi.org/10.1021/jacs.6b07830 (Year: 2016).*
Keneford; J. Chem. Soc., 1952, 2595-2602. https://doi.org/10.1039/JR9520002595 (Year: 1952).*
Neelakantan; J. Med. Chem. 2017, 60, 12, 5015-5028. https://doi.org/10.1021/acs.jmedchem.7b00389 (Year: 2017).*
Neelakantan; Biochemistry 2017, 56, 6, 824-832. https://doi.org/10.1021/acs.biochem.6b01215 (Year: 2017).*
Plakogiannis; J. Med. Chem. 1971, 14, 5, 430-432. https://doi.org/10.1021/jm00287a013 (Year: 1971).*
Van Haren; Biochemistry 2016, 55, 5307-5315. https://doi.org/10.1021/acs.biochem.6b00733 (Year: 2016).*

* cited by examiner

*Primary Examiner* — Daniel R Carcanague
(74) *Attorney, Agent, or Firm* — HYLTON-RODIC LAW PLLC

(57) ABSTRACT

The present invention relates to quinoline derived small molecule inhibitors of nicotinamide N-methyltransferase (NNMT), the preparation thereof and uses thereof.

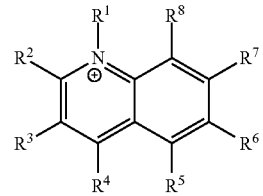

30 Claims, 19 Drawing Sheets

5-amino-1-methylquinolin-1-ium iodide (1j)

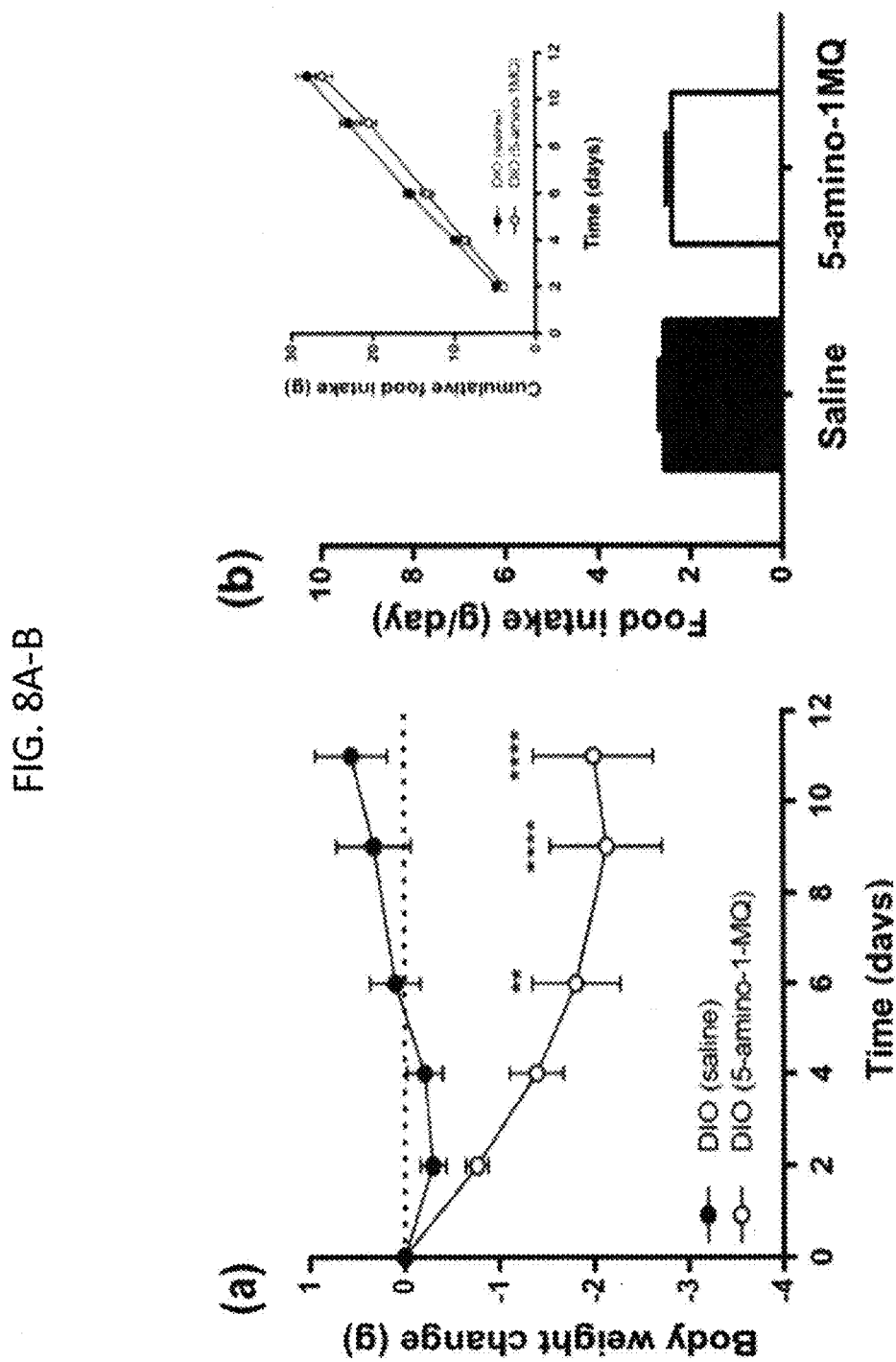
FIG. 8A-B

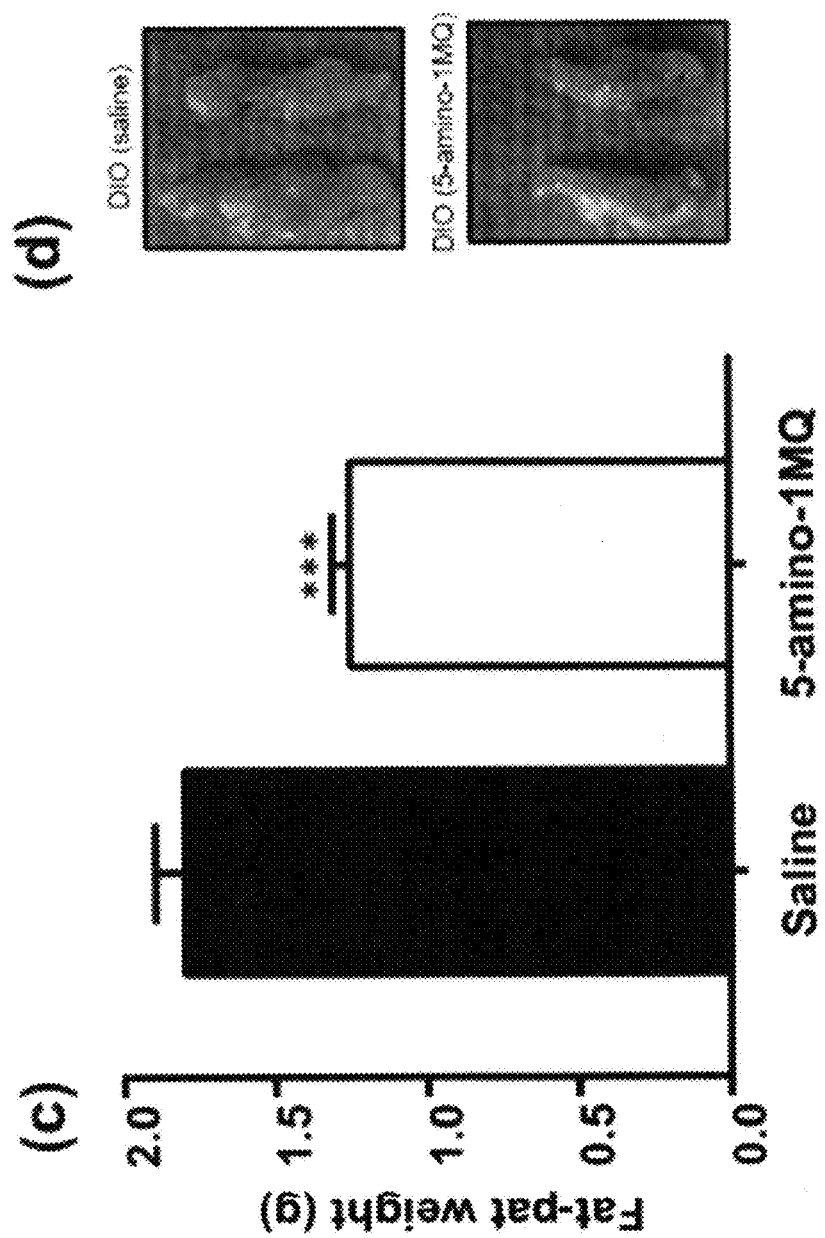
FIG. 8C-D

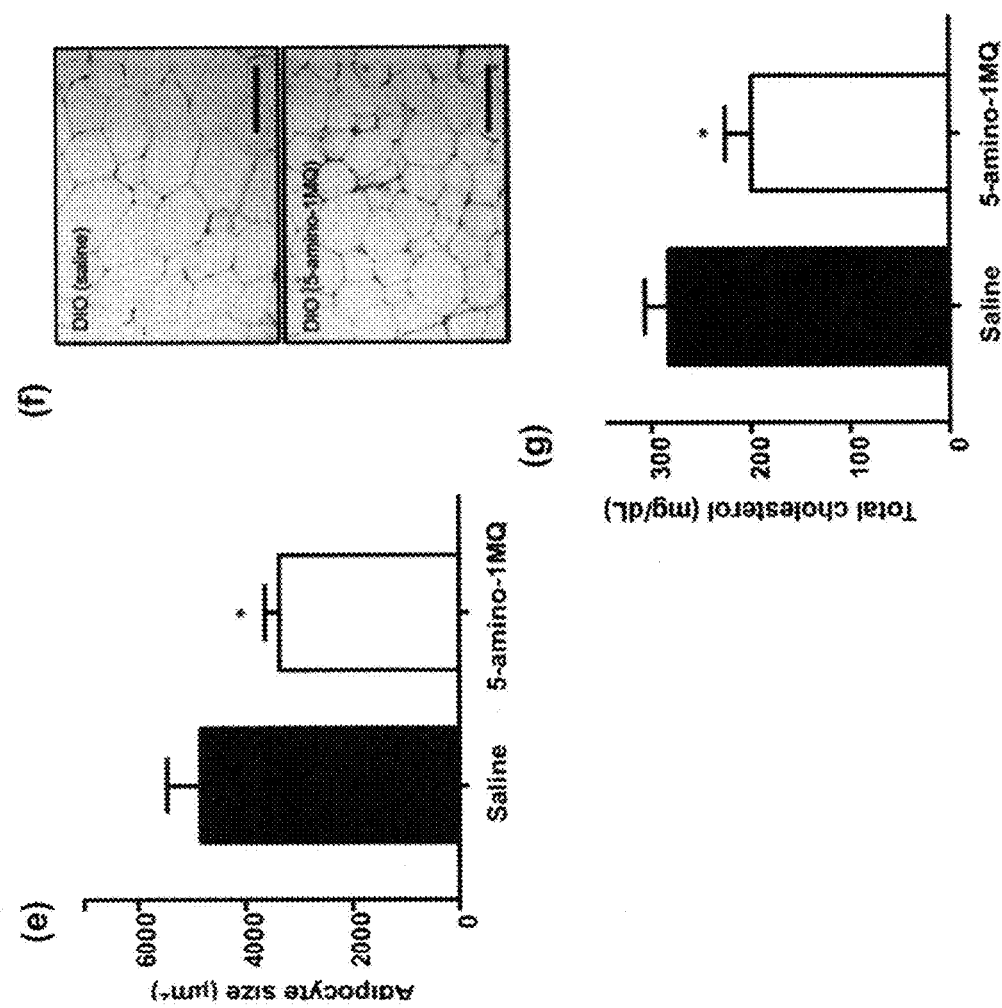
FIG. 8E-G

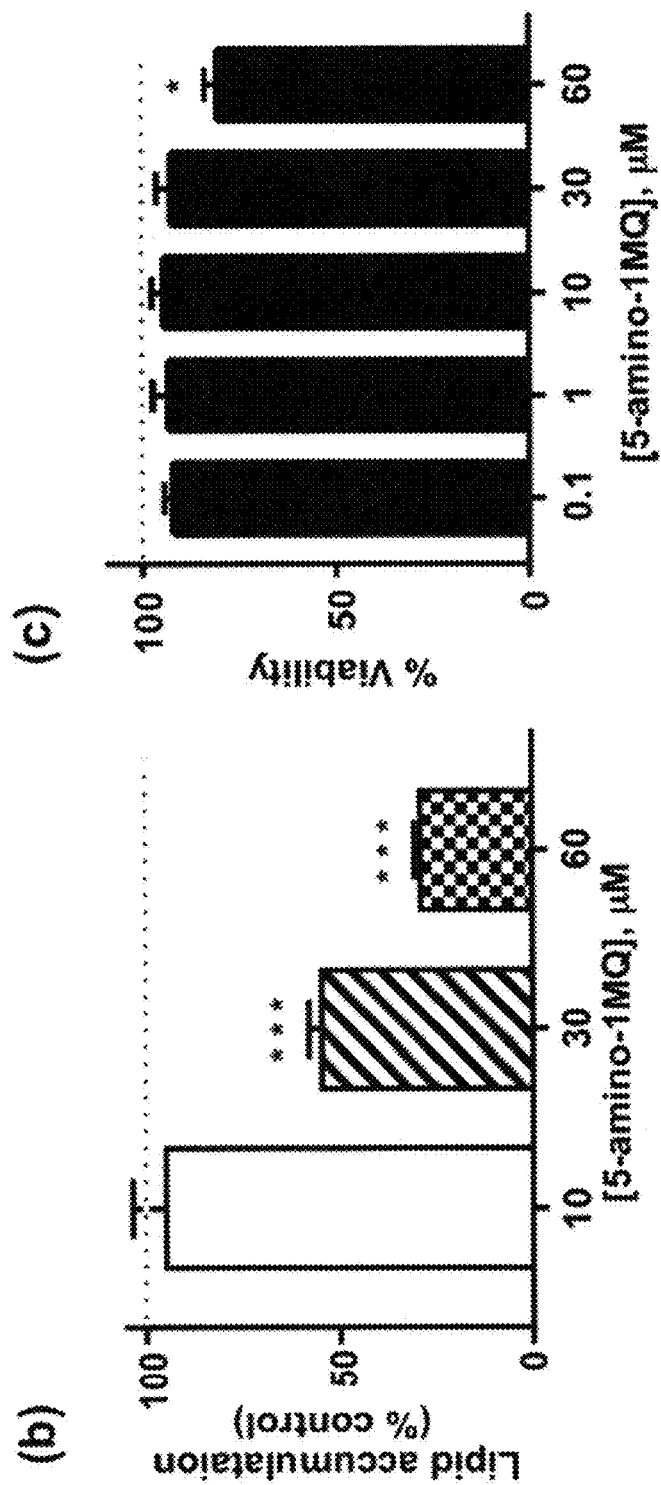
FIG. 9B-C

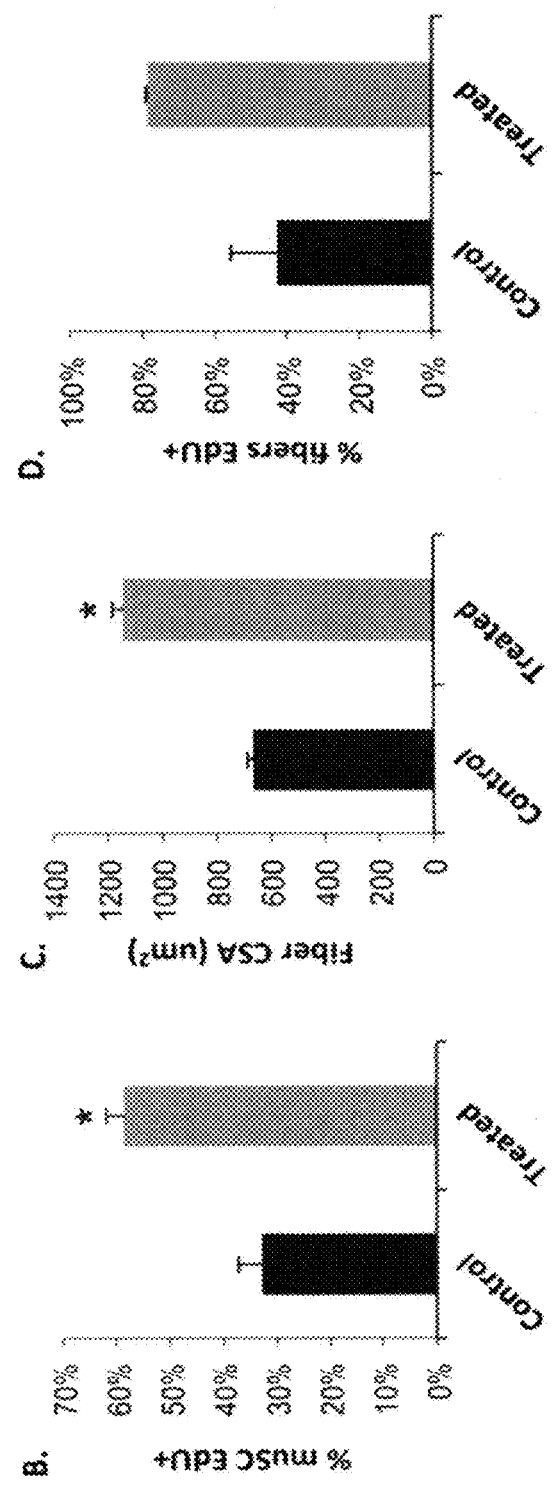
FIG. 11B-D

QUINOLINE DERIVED SMALL MOLECULE INHIBITORS OF NICOTINAMIDE N-METHYLTRANSFERASE (NNMT) AND USES THEREOF

CROSS-REFERENCE TO RELATED APPLICATIONS

This application is a Continuation of U.S. Non-Provisional application Ser. No. 16/499,228, filed Sep. 27, 2019, which claims priority to U.S. National Phase application of International Application No. PCT/US18/25134, filed Mar. 29, 2018, which claims the benefit of U.S. Provisional Appl. No. 62/479,256, filed Mar. 30, 2017, and U.S. Provisional Appl. No. 62/559,417, filed Sep. 15, 2017. The content of the aforesaid applications are relied upon and are incorporated by reference herein in their entirety.

STATEMENT OF FEDERALLY SPONSORED RESEARCH AND DEVELOPMENT

This invention was made with government support under Grant No. W81XWH-15-1-0372 awarded by the U.S. Department of Defense (DOD). The government has certain rights in the invention.

FIELD OF THE INVENTION

The field of the invention relates generally to quinoline derived small molecule inhibitors of nicotinamide N-methyltransferase (NNMT), the preparation thereof, and the uses thereof.

BACKGROUND

Nicotinamide N-methyltransferase (NNMT) is a key enzyme located in the cytosolic milieu that catalyzes the transfer of methyl group from the co-factor S-(5'-Adenosyl)-L-methionine (SAM) to substrates such as nicotinamide (NCA), pyridine, and related analogs, such as quinoline, isoquinoline, and the aliphatic amine 1,2,3,4 tetrahydroisoquinoline.

NNMT directly regulates the detoxification of endogenous and exogenous drugs/xenobiotics by the formation of methylated metabolic products, such as 1-methyl nicotinamide (1-MNA), methylated pyridiniums, and methylated related analogs. Given its primary metabolizing function, NNMT is predominantly expressed in the liver, but modest levels of the enzyme are also present in other tissues, including the adipose tissue, kidney, brain, lung, heart, and muscle.

Enhanced expression and enzymatic activity of NNMT has been linked to a number of chronic disease conditions making it a relevant target for drug development. For example, several studies support a causal relationship between augmented NNMT activity in cancer cells and tumor proliferation/progression in a variety of cancerous states with potential implications for NNMT as a biomarker for cancer prognosis and a relevant target for anti-cancer therapeutic development. NNMT activity is also upregulated in the brain tissue of patients with Parkinson's disease (See e.g., K. Aoyama, K. Matsubara, M. Kondo, Y. Murakawa, M Suno, K. Yamashita, S. Yamaguchi, S. Kobayashi. *Nicotinamide-N-methyltransferase is higher in the lumbar cerebrospinal fluid of patients with Parkinson's disease. Neurosci Lett.*, 298, 78-80, 2001; R. B. Parsons, M. L. Smith, A. C. Williams, R. H. Waring, D. B. Ramsden. *Expression of nicotinamide N-methyltransferase (E.C.2.1.1.1) in the Parkinsonian brain. J. Neuropathol. Exp. Neurol.*, 61, 111-124, 2002) leading to excess production of N-methylpyridinium ions in the brain that act as neurotoxins linked to the pathogenesis of neurodegeneration (See e.g., Herraiz T. *N-methyltetrahydropyridines and pyridinium cations as toxins and comparison with naturally-occurring alkaloids. Food Chem Toxicol.* 97, 23-39, 2016).

Furthermore, it has been reported that in both animals and humans NNMT expression and activity is enhanced in obesity and related chronic metabolic conditions (e.g., type-2 diabetes). In fact, knockdown of the NNMT protein in the adipose tissue and liver using antisense oligonucleotides limited body weight gain in mice fed high fat diet, causing substantial fat mass reduction via increased energy expenditure.

Additionally, NNMT is known to modulate intracellular metabolite turnover in the methionine-homocysteine cycle and the nicotinamide adenine dinucleotide (NAD+) synthesis pathways critical for cellular energy expenditure. Therefore, targeted small molecule inhibitors of the NNMT could be significantly beneficial as molecular probes for mechanistic investigations and for the development of therapeutics for the treatment of metabolic and chronic disease conditions that are characterized by abnormal NNMT activity.

Finally, the ability of stem cells to self-renew and their capability to regenerate all tissues in the body makes understanding their biological mechanism an important goal. In fact, it was recently found that NNMT participates in regulating stem cell pluripotency in hESCs. See e.g., Sperber, H., et al., *Nat Cell Biol.* 17: 1523-1535 (2015). In particular, it was found that NNMT is required for low SAM levels and H3K27me3 repressive state. See e.g., Sperber, H., et al., *Nat Cell Biol.* 17: 1523-1535 (2015). This link between NNMT and stem cells makes development of therapeutics to treat regenerative-related diseases a relevant target.

Furthermore, several recent studies have showed modest increases in intracellular NAD+, achieved through nutraceutical supplements, dramatically increased muscle stem cell (muSC) activity in aged mice and the mdx mouse model of Duchenne MD.

In summary, the fact that NNMT plays a role in a number of diseases/conditions makes development of NNMT inhibitors an important path to developing therapeutics to treat various diseases/conditions.

This background information is provided for the purpose of making information believed by the applicant to be of possible relevance to the present invention. No admission is necessarily intended, nor should it be construed, that any of the preceding information constitutes prior art against the present invention.

SUMMARY

The inventors have discovered certain novel small molecule NNMT inhibitors and have developed methods for preparing these molecules.

The inventors have also discovered that NNMT inhibitors may be used to inhibit NNMT and to treat related diseases or conditions. Further, the inventors have discovered that NNMT inhibitors may be used for muscular therapy.

One aspect of the invention pertains to small molecule quinoline derived cations of Formula I, wherein:

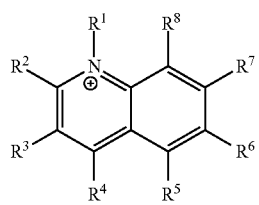

Formula I $R^1$ is $C_{1-4}$ alkyl;
$R^2$, $R^3$, $R^4$, and $R^5$ are independently selected from the group consisting of: H, $C_{1-4}$ alkyl, halogen-substituted $C_{1-4}$ alkyl, $NR^9R^{10}$, and CN;
$R^6$ is H or halogen;
$R^7$ is H, methyl, or $NR^{11}R^{12}$; and
$R^8$ is H, $C_{1-4}$ alkyl, halogen-substituted $C_{1-4}$ alkyl;
$R^9$, $R^{10}$, $R^{11}$, and $R^{12}$ are independently selected from H and $C_{1-4}$ alkyl;
wherein the compound has at least two non-hydrogen substituents at positions $R^2$-$R^8$;
and wherein at least one of the non-hydrogen substituents at positions $R^2$-$R^8$ is $NH_2$.

Another aspect of the invention pertains to small molecule quinoline derived cations of Formula IA, wherein:

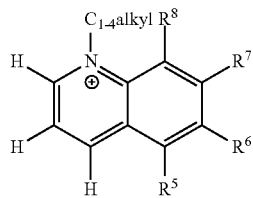

Formula IA the cation of Formula IA includes two or more non-hydrogen substituents, and wherein:
$R^5$ is H or $NH_2$,
$R^6$ is H or F;
$R^7$ is H or $NH_2$,
$R^8$ is H or methyl.

A further aspect of the invention pertains to use of the cations of the invention to inhibit NNMT and to treat related diseases or conditions. In some embodiments, the invention encompasses use of one or more cations of the invention to inhibit NNMT in vitro or in vivo by contacting a cell expressing NNMT.

In some embodiments, the invention encompasses use of one or more cations of the invention to treat obesity or related chronic metabolic condition, including metabolic syndrome, pre-diabetes, type-2 diabetes, obesity-linked diseases (e.g., non-alcoholic fatty liver disease, non-alcoholic steatohepatitis, CVDs, and the like).

In some embodiments, the invention encompasses use of one or more cations of the invention to treat an NNMT-expressing cancer. In further embodiments, the invention encompasses use of one or more cations of the invention to treat tumorigenesis and metastasis of NNMT-positive cancers.

In some embodiments, the invention encompasses use of one or more cations of the invention to treat Parkinson and related neurological diseases.

In some embodiments, the invention encompasses use of one or more cations of the invention to modulate stem cell differentiation.

One aspect of the invention pertains to the use of small molecule quinoline derived cations of Formula I for muscular therapy, wherein:

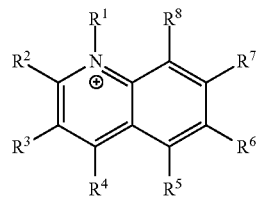

Formula I $R^1$ is $C_{1-4}$ alkyl;
$R^2$, $R^3$, $R^4$, and $R^5$ are independently selected from the group consisting of: H, $C_{1-4}$ alkyl, halogen-substituted $C_{1-4}$ alkyl, $NR^9R^{10}$, and CN;
$R^6$ is H or halogen;
$R^7$ is H, methyl, or $NR^{11}R^{12}$; and
$R^8$ is H, $C_{1-4}$ alkyl, halogen-substituted $C_{1-4}$ alkyl;
$R^9$, $R^{10}$, $R^{11}$, and $R^{12}$ are independently selected from H and $C_{1-4}$ alkyl;
wherein the compound has at least two non-hydrogen substituents at positions $R^2$-$R^8$;
and wherein at least one of the non-hydrogen substituents at positions $R^2$-$R^8$ is $NH_2$.

Another aspect of the invention pertains to the use of small molecule quinoline derived cations of Formula IA for muscular therapy, wherein:

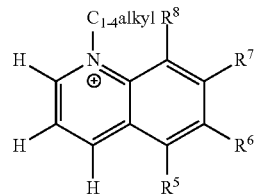

Formula IA the cation of Formula IA includes two or more non-hydrogen substituents, and wherein:
$R^5$ is H or $NH_2$,
$R^6$ is H or F;
$R^7$ is H or $NH_2$,
$R^8$ is H or methyl.

BRIEF DESCRIPTION OF THE FIGURES

FIG. 8A-G. Effects of saline or NNMT inhibitor (5-amino-1MQ, 20 mg/kg, t.i.d.) administered SC over a 11-day period in DIO mice on body weight changes from baseline (a), average food intake (g/day) and cumulative food intake across 11-days [inset] (b), epididymal fat-pad weight (c), size of the EWAT (representative images) (d), adipocyte size (µm2) determined in mean number of 20.7±1.8 (DIO, saline) and 28.6±2.3 adipocytes (DIO, 5-amino-1MQ) (e), representative H&E stained images of saline- and 5-amino-1MQ-treated DIO EWAT tissue (scale bar=200 m) (f), and total plasma cholesterol levels following a 4-h fasting period (mg/gL) (g). All data points represent the mean values in n=9 mice/group±SEM. *, P<0.05; , P<0.01, *, P<0.0001 vs. saline-treated DIO analyzed by unpaired Student's t-test or repeated measures two-way ANOVA with multiple comparisons posthoc tests where applicable.

FIG. 9A-C. Effects of 5-amino-1MQ on lipogenesis in differentiating 3T3-L1 cells. Representative images of culture plates (top panels) and microscopic images (20× magnification; scale bar=50 m; bottom panels) following oil red O staining of lipid droplets in the control untreated and 5-amino-1MQ (15, 30, and 60 µM)-treated adipocytes (treatment continued throughout the period of differentiation) (a). Lipid accumulation determined by quantification of oil red O staining in 5-amino-1MQ (15, 30, and 60 µM)-treated adipocytes; data points represent average normalized (% untreated control) values (±SEM) in treated adipocyte samples (n=2 replicates per experiment; experiment performed 3 times) (b). Viability of 3T3-L1 cells treated with 5-amino-1MQ (0.1-60 µM); data points represent average normalized (% untreated control) values (±SEM) in treated 3T3-L1 samples (n=3 replicates per experiment; experiment performed 3 times). ***, P=0.0001 vs. untreated adipocytes (0 µM); *, P<0.01 vs. untreated 3T3-L1 cells analyzed by one-way ANOVA with Dunnett's posthoc tests (c).

FIGS. 11A to 11D. Treatment with NNMT inhibitor doubled muscle fiber cross sectional area and enhance muscle stem cell (muSC) activation and integration into regenerating muscle fibers following injury in aged (>24 mo old) mice. Greater prevalence of EdU+/Pax7+ muSC (white arrows), EdU+ myonuclei (red arrows), and larger mean fiber cross-sectional area (CSA; denoted by dotted circle around the laminin staining) were clearly noted in treated animals (FIG. 11A); scale bar=50 um; *, p<0.05 versus control; % Edu+ positive muSC had doubled in treated mice (FIG. 11B); Fiber cross-sectional area (CSA) doubled in treated mice vs. control (FIG. 11C); % Edu+ fibers increased in treated mice, indicative of increased fusion into damaged myofibers (FIG. 11D).

DETAILED DESCRIPTION

Figure 1:
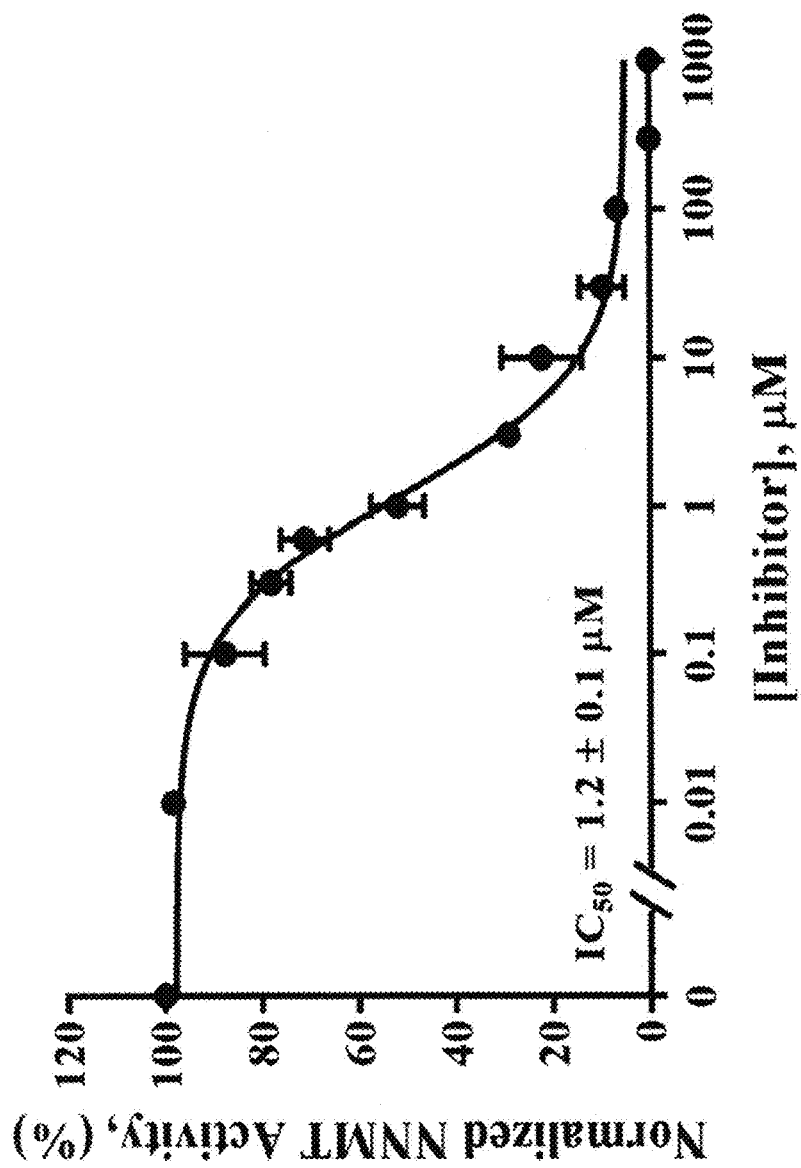
FIG. 1. Normalized response curves for NNMT inhibitor 1j (5-amino-1-methylquinolinium), a quinolinium derivative. Data points represent average and standard deviation of normalized NNMT activity [data points normalized to no inhibitor condition (0 μM) within each experiment, n=5 experiments]. The goodness-of-fit R2 between the fitted curves and data was 0.97.

It is to be understood that both the foregoing general description of the invention and the following detailed description are exemplary, and thus do not restrict the scope of the invention.

Definitions

For the purposes of promoting an understanding of the principles of the invention, reference will now be made to certain embodiments and specific language will be used to describe the same. It will nevertheless be understood that no limitation of the scope of the invention is thereby intended, and alterations and modifications in the illustrated invention, and further applications of the principles of the invention as illustrated therein are herein contemplated as would normally occur to one skilled in the art to which the invention relates.

Unless defined otherwise, all technical and scientific terms used herein have the same meaning as commonly understood by one of ordinary skill in the art to which this invention pertains.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used).

The use of "or" means "and/or" unless stated otherwise.

The use of "a" herein means "one or more" unless stated otherwise or where the use of "one or more" is clearly inappropriate.

The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein, the term "about" refers to a ±10% variation from the nominal value. It is to be understood that such a variation is always included in any given value provided herein, whether or not it is specifically referred to.

The term "alkyl" as used herein by itself or as part of another group refers to both straight and branched chain radicals. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons (also referred to as "$C_{1-4}$ alkyl" or "$C_{1-4}$ alkyl"). The term "alkyl" may include methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, and dodecyl.

The term "alkylene" as used herein refers to straight and branched chain alkyl linking groups, i.e., an alkyl group that links one group to another group in a molecule. In some embodiments, the term "alkylene" may include —$(CH_2)_n$- where n is 2-8.

The term "aryl" refers to an aromatic group having at least one carbocyclic aromatic group or heterocyclic aromatic group, which may be unsubstituted or substituted by one or more groups selected from halogen, haloalkyl, hydroxy, alkoxy, carbonyl, alkylamido, nitro, amino, dialkylamino, carboxy, thio or thioalkyl. Non-limiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like.

An "amino" group refers to an —NH2 group.

An "amido" group refers to an —$CONH_2$ group. An alkylamido group refers to an —CONHR group wherein R is as defined above. A dialkylamido group refers to an —CONRR' group wherein R and R' are as defined above.

The term "halogen" or "halo" as used herein by itself or as part of another group refers to chlorine, bromine, fluorine or iodine.

The term "hydroxy" or "hydroxyl" as used herein by itself or as part of another group refers to an —OH group.

An "alkoxy" group refers to an —O-alkyl group wherein "alkyl" is as defined above.

A "thio" group refers to an —SH group.

An "alkylthio" group refers to an —SR group wherein R is alkyl as defined above.

The term "heteroaryl" as used herein refers to groups having 5 to 14 ring atoms; 6, 10 or 14 7π-electrons shared in a cyclic array; and containing carbon atoms and 1, 2 or 3 oxygen, nitrogen or sulfur heteroatoms. The heteroaryl moiety may be unsubstituted or substituted by one or more groups selected from halogen, haloalkyl, hydroxy, alkoxy, carbonyl, alkylamido, nitro, amino, dialkylamino, carboxy, thio or thioalkyl. Examples of heteroaryl groups include thienyl, imadizolyl, oxadiazolyl, isoxazolyl, triazolyl, pyridyl, pyrimidinyl, pyridazinyl, furyl, pyranyl, thianthrenyl, pyrazolyl, pyrazinyl, indolizinyl, isoindolyl, isobenzofuranyl, benzoxazolyl, xanthenyl, 2H-pyrrolyl, pyrrolyl, 3H-indolyl, indolyl, indazolyl, purinyl, 4H-quinolizinyl, isoquinolyl, quinolyl, phthalazinyl, naphthyridinyl, quinazolinyl, phenanthridinyl, acridinyl, perimidinyl, phenanthrolinyl, phenazinyl, isothiazolyl, phenothiazinyl, isoxazolyl, furazanyl, and phenoxazinyl groups. Especially preferred heteroaryl groups include 1,2,3-triazole, 1,2,4-triazole, 5-amino 1,2,4-triazole, imidazole, oxazole, isoxazole, 1,2,3-oxadiazole, 1,2,4-oxadiazole, 3-amino-1,2,4-oxadiazole, 1,2,5-oxadiazole, 1,3,4-oxadiazole, pyridine, and 2-aminopyridine.

The term "heterocycle" or "heterocyclic ring", as used herein except where noted, represents a stable 5- to 7-membered monocyclic-, or stable 7- to 11-membered bicyclic heterocyclic ring system, any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Rings may contain one oxygen or sulfur, one to three nitrogen atoms, or one oxygen or sulfur combined with one or two nitrogen atoms. The heterocyclic ring may be attached at any heteroatom or carbon atom that results in the creation of a stable structure. Further, "heterocycle" or "heterocyclic ring" moiety may be unsubstituted or substituted by one or more groups selected from halogen, haloalkyl, hydroxy, alkoxy, carbonyl, alkylamido, nitro, amino, dialkylamino, carboxy, thio or thioalkyl. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

The term "alkylamino" as used herein by itself or as part of another group refers to an amino group which is substituted with one alkyl group having from 1 to 6 carbon atoms. The term "dialkylamino" as used herein by itself or as part of another group refers to an amino group which is substituted with two alkyl groups, each having from 1 to 6 carbon atoms.

The term "alkylthio" as used herein by itself or as part of another group refers to an thio group which is substituted with one alkyl group having from 1 to 6 carbon atoms.

As used herein, the terms "cell", "cells", and "a cell expressing NNMT" (as used interchangeably herein) refer to one or cells, from any animal, which expresses NNMT, such as, without limitation, rat, mice, monkey, horse, dog, cat, and human. For example, and without limitation, cells can be progenitor cells, such as stem cells, or differentiated cells, such as endothelial cells, smooth muscle cells. In certain embodiments, cells for medical procedures can be obtained from the patient for autologous procedures or from other donors for allogeneic procedures.

A "therapeutically effective amount" is an amount sufficient to decrease, prevent or ameliorate the symptoms associated with a medical condition.

The term "non-hydrogen substituent" refers to a substituent that is not made up solely of hydrogen. Examples of non-hydrogen substituents includes halogen, C1-4 alkyl, halogen-substituted C1-4 alkyl, $NR^9R^{10}$, $NR^{11}R^{12}$, and CN. In some embodiments, non-hydrogen substituent includes methyl. In further embodiments, non-hydrogen substituent includes fluoride (F). In further embodiments, non-hydrogen substituent includes $NH_2$.

The terms "compound", "cation", "small molecule cation", and "quinoline derived small molecule cation" have been used interchangeably throughout the application to refer to embodiments of the invention and doing so is not meant in any way to limit the scope of the invention.

The term "muscular therapy" as used herein refers to contacting one or more cells of a subject with one or more NNMT inhibitors to treat and/or prevent muscular disorders; improve neuromuscular function; reduce the time required to restore neuromuscular function; prevent neuromuscular injury; and/or improve muscle regeneration. This term also encompasses administration of NNMT inhibitors to treat and/or prevent muscular disorders; improve neuromuscular function; reduce the time required to restore neuromuscular function; prevent neuromuscular injury; and/or improve muscle regeneration.

The term "NNMT inhibitors" as used herein refers small molecule chemical entities that inhibit the enzymatic activity of NNMT, and includes the compounds of Formula I and Formula IA as well as compounds in Tables 1-3.

The term "administering" or "administration" refers to contacting one or more cells of a subject, (including human, horse, cat, dog, monkey, rat, and mice) with one or more NNMT inhibitors. In some embodiments administration may occur in vitro. In further embodiments, administration may occur in vivo.

It is to be understood that both the foregoing description are exemplary, and thus do not restrict the scope of the invention.

Compounds of Formula I

The inventors surprisingly discovered a genus of quinoline derived cations of Formula I, which may be used to inhibit NNMT. In some embodiments, the invention encompasses cations of Formula I, wherein:

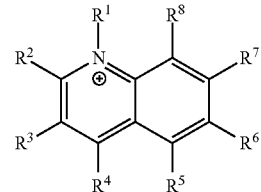

Formula I $R^1$ is $C_{1-4}$ alkyl;
$R^2$, $R^3$, $R^4$, and $R^5$ are independently selected from the group consisting of: H, C1-4 alkyl, halogen-substituted $C_{1-4}$ alkyl, $NR^9R^{10}$, and CN;
$R^6$ is H or halogen;
$R^7$ is H, methyl, or $NR^{11}R^{12}$; and
$R^8$ is H, $C_{1-4}$ alkyl, halogen-substituted $C_{1-4}$ alkyl;
$R^9$, $R^{10}$, $R^{11}$, and $R^{12}$ are independently selected from H and $C_{1-4}$ alkyl;
wherein the compound has at least two non-hydrogen substituents at positions $R^2$-$R^8$;
and wherein at least one of the non-hydrogen substituents at positions $R^2$-$R^8$ is $NH_2$.

In further embodiments, $R^1$ may be methyl or ethyl.
In further embodiments, $R^1$ is methyl.
In some embodiments, at least one of $R^2$ and $R^3$ is $NH_2$.
In some embodiments, $R^5$ is $NH_2$.
In some embodiments, $R^2$, $R^3$, and $R^4$ are hydrogen.
In some embodiments, $R^6$ is halogen.
In some embodiments, $R^6$ is F.
In some embodiments, $R^7$ is $NH_2$.
In some embodiments, $R^8$ is methyl or $CF_3$.
In some embodiments, $R^8$ is methyl.
In further embodiments, the invention encompasses a cation of Formula IA, wherein:

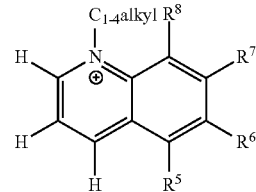

Formula IA the cation of Formula IA includes two or more non-hydrogen substituents at positions $R^2$-$R^8$, and wherein:
$R^5$ is H or $NH_2$,
$R^6$ is H or F;
$R^7$ is H or $NH_2$,
$R^8$ is H or methyl.

In some embodiments of Formula IA, $R^1$ is methyl or ethyl.
In some embodiments of Formula IA, $R^6$ is F.
In certain embodiments, the cation of Formula IA is one of:

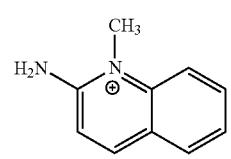

1c

-continued

1c'

1f

1f'

1l

1l'

1m

1m'

2j

2j'

2m

2m'

2k

2k'

2l

2l'

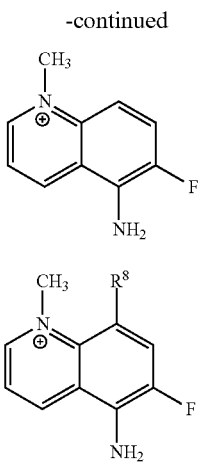

2aa

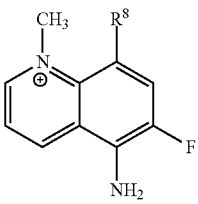

2aa' wherein:
R⁵ is H or NH₂;
R⁶ is H or F; and
R⁸ is H or methyl.

In certain embodiments, the small molecule cations of the invention may be accompanied by a counter anion ($X^-$). In some embodiments, the counter ion may be chosen from sulfonate (e.g., trifluoromethanesulfonate, mesylate, tosylate, besylate, and the like); halide (e.g., fluoride, bromide, chloride or iodide); acetate; sulfate; bisulfate; nitrate; oxalate; valerate; oleate; palmitate; stearate; laurate; borate; benzoate; lactate; phosphate; citrate; maleate; fumarate; succinate; tartrate; glucoheptonate; and lactobionate.

Another aspect of the invention pertains generally to the use of the cations of the invention to inhibit NNMT and diseases or conditions involving NNMT. NNMT has been linked to a number of chronic diseases/conditions. For example, several studies support a causal relationship between augmented NNMT activity in cancer cells and tumor proliferation/progression in a variety of cancerous states with potential implications for NNMT as a biomarker for cancer prognosis and a relevant target for anti-cancer therapeutic development. It was recently found, for instance, that NNMT was preferentially expressed by mesenchymal glioblastoma stem cells (GSCs). See e.g., FIGS. 5 and 9 of Jung, J., et al., *Nicotinamide metabolism regulates glioblastoma stem cell maintenance* JCI Insight, 2:1-23 (2017).

NNMT activity also plays a role in Parkinson's disease and in modulating stem cell differentiation. Furthermore, emerging reports in both animals and humans indicate that NNMT plays a role in obesity and related chronic metabolic conditions (e.g., type-2 diabetes).

In some embodiments, the invention encompasses a method of inhibiting NNMT in vitro or in vivo by contacting a cell expressing NNMT with one or more cations of the invention. In further embodiments, the invention encompasses a method of inhibiting NNMT in vitro or in vivo by contacting a cell expressing NNMT with one or more cations chosen from 1c, 1f, 1l, 1m, 2j, 2k, 2l, 2m, 2aa, 1c', 1f', 1l', 1m', 2j', 2k', 2l', 2m', and 2aa'.

In further embodiments, the invention encompasses a method of inhibiting NNMT in vitro or in vivo by contacting a cell expressing NNMT with one or more cations chosen from Tables 1, 2, 3a, and 3b. In further embodiments, the invention encompasses a method of inhibiting NNMT in vitro or in vivo by contacting a cell expressing NNMT with one or more cations of the invention and with one or more cations chosen from Tables 3a and 3b. In one aspect of the invention, one or more cations of the invention is contacted with a cell expressing NNMT concurrently with one or more cations chosen from Tables 3a and 3b. In another aspect of the invention, one or more cations of the invention is contacted with a cell expressing NNMT followed by contacting said cell expressing NNMT with one or more cations chosen from Tables 3a and 3b. In a further aspect of the invention, one or more cations chosen from Tables 3a and 3b is contacted with a cell expressing NNMT followed by contacting said cell expressing NNMT with one or more cations of the invention.

In some embodiments, the invention encompasses a method of treating obesity or related chronic metabolic condition by administering a therapeutically effective amount of one or more cations of the invention. In further embodiments, the invention encompasses a method of treating obesity or related chronic metabolic condition by administering a therapeutically effective amount of one or more cations chosen from 1c, 1f, 1l, 1m, 2j, 2k, 2l, 2m, 2aa, 1c', 1f', 1l', 1m', 2j', 2k', 2l', 2m', and 2aa'.

In further embodiments, the invention encompasses a method of treating obesity or related chronic metabolic condition by administering a therapeutically effective amount of one or more cations chosen from Tables 1, 2, 3a, and 3b. In further embodiments, the invention encompasses a method of treating obesity or related chronic metabolic condition by administering a therapeutically effective amount of one or more cations of the invention and one or more cations chosen from Tables 3a and 3b. One aspect of the invention pertains to treating obesity or related chronic metabolic condition by administering a therapeutically effective amount of one or more cations of the invention with concurrent administration of one or more cations chosen from Tables 3a and 3b. Another aspect of the invention pertains to treating obesity or related chronic metabolic condition by administering a therapeutically effective amount of one or more cations of the invention followed by administration of one or more cations chosen from Tables 3a and 3b. A further aspect of the invention pertains to treating obesity or related chronic metabolic condition by administering a therapeutically effective amount of one or more cations chosen from Tables 3a and 3b followed by the administration of one or more cations of the invention.

In certain embodiments, the invention encompasses a method of treating an NNMT-expressing cancer, such as glioblastoma, by administering a therapeutically effective amount of one or more cations of the invention. In further embodiments, the invention encompasses a method of treating an NNMT-expressing cancer such as glioblastoma, by administering a therapeutically effective amount of one or more cations chosen from 1c, 1f, 1l, 1m, 2j, 2k, 2l, 2m, 2aa, 1c', 1f', 1l', 1m', 2j', 2k', 2l', 2m', and 2aa'.

In further embodiments, the invention encompasses a method of treating an NNMT-expressing cancer, such as glioblastoma, by administering a therapeutically effective amount of one or more cations chosen from Tables 1, 2, 3a, and 3b. In further embodiments, the invention encompasses a method of treating an NNMT-expressing cancer by administering a therapeutically effective amount of one or more cations of the invention and one or more cations chosen from Tables 3a and 3b. One aspect of the invention pertains to treating an NNMT-expressing cancer, such as glioblastoma, by administering a therapeutically effective amount of one or more cations of the invention with concurrent administration of one or more cations chosen from Tables 3a and 3b. Another aspect of the invention pertains to treating an NNMT-expressing cancer, such as glioblastoma, by administering a therapeutically effective amount of one or more cations of the invention followed by administration of one or more cations chosen from Tables 3a and 3b. A further aspect of the invention pertains to treating an NNMT-expressing cancer, such as glioblastoma, by administering a therapeutically effective amount of one or more cations chosen from Tables 3a and 3b followed by the administration of one or more cations of the invention.

In certain embodiments, the invention encompasses a method of treating Parkinson and related neurological diseases by administering a therapeutically effective amount of one or more cations of the invention. In further embodiments, the invention encompasses a method of treating Parkinson and related neurological diseases by administering a therapeutically effective amount of one or more cations chosen from 1c, 1f, 1l, 1m, 2j, 2k, 2l, 2m, 2aa, 1c', 1f', 1l', 1m', 2j', 2k', 2l', 2m', and 2aa'.

In further embodiments, the invention encompasses a method of treating Parkinson and related neurological diseases by administering a therapeutically effective amount of one or more cations chosen from Tables 1, 2, 3a, and 3b. In further embodiments, the invention encompasses a method of treating Parkinson and related neurological diseases by administering a therapeutically effective amount of one or more cations of the invention and one or more cations chosen from Tables 3a and 3b. One aspect of the invention pertains to treating Parkinson and related neurological diseases by administering a therapeutically effective amount of one or more cations of the invention with concurrent administration of one or more cations chosen from Tables 3a and 3b. Another aspect of the invention pertains to treating Parkinson and related neurological diseases by administering a therapeutically effective amount of one or more cations of the invention followed by administration of one or more cations chosen from Tables 3a and 3b. A further aspect of the invention pertains to treating Parkinson and related neurological diseases by administering a therapeutically effective amount of one or more cations chosen from Tables 3a and 3b followed by the administration of one or more cations of the invention.

In some embodiments, the invention encompasses a method of modulating stem cell differentiation by contacting a stem cell expressing NNMT with one or more cations of the invention. In further embodiments, the invention encompasses a method of modulating stem cell differentiation by contacting a stem cell expressing NNMT with one or more cations chosen from 1c, 1f, 1l, 1m, 2j, 2k, 2l, 2m, 2aa, 1c', 1f', 1l', 1m', 2j', 2k', 2l', 2m', and 2aa'.

In further embodiments, the invention encompasses a method of modulating stem cell differentiation by contacting a stem cell expressing NNMT with one or more cations chosen from Tables 1, 2, 3a, and 3b. In further embodiments, the invention encompasses a method of modulating stem cell differentiation by contacting a stem cell expressing NNMT with one or more cations of the invention and with one or more cations chosen from Tables 3a and 3b. In one aspect of the invention, one or more cations of the invention is contacted with a stem cell expressing NNMT concurrently with one or more cations chosen from Tables 3a and 3b. In another aspect of the invention, one or more cations of the invention is contacted with a stem cell expressing NNMT followed by contacting said stem cell expressing NNMT with one or more cations chosen from Tables 3a and 3b. In a further aspect of the invention, one or more cations chosen from Tables 3a and 3b is contacted with a stem cell expressing NNMT followed by contacting said stem cell expressing NNMT with one or more cations of the invention.

Synthesis of Cations of Formulas I and IA

The description of preparation of certain embodiments of the invention is meant to be exemplary of certain embodiments of the invention. The reagents and reactants used for synthetic conversions outlined herein and below is merely exemplary. The invention contemplates using the same or different reagents discussed herein to achieve preparation of the cations of the invention.

Certain cations of Formula I and IA can be prepared via N-alkylation of a substituted quinoline derivative. In some embodiments, preparation of certain cations of Formulas I and IA may occur by alkylating the N-positions of the quinoline scaffold using, for example, iodomethane or methyl trifluoromethanesulfonate (see Scheme 1).

Scheme 1. Synthetic Route for Certain Cations of the Invention[a]

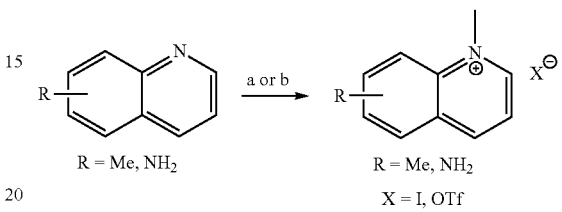

R = Me, NH$_2$      R = Me, NH$_2$
                                    X = I, OTf

[a]Reagents and conditions: (a) iodomethane, isopropanol, 90° C., 12 h; (b) MeOTf, toluene, 100° C., 12 h.

In some embodiments, preparation of certain cations of the invention may occur via reductive amination followed by alkylation.

Scheme 2. Synthesis of certain
C3-amino-alkylated quinolinium derivatives of the invention[a]

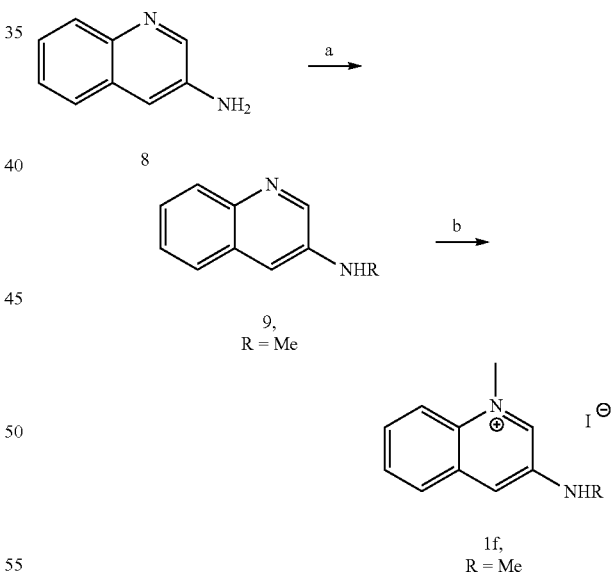

[a]Reagents and conditions:
(a) triethyl orthoformate, TFA, 125° C., 12 h then NaBH$_4$, EtOH, room temperature, 12 h;
(b) MeI, IPA, 90° C., 12 h.

Certain cations of the invention may be prepared via the two-step process outlined in Scheme 2, as exemplified with the preparation of cation 1f. Specifically, alkylation of a C3-amino-quinoline derived precursor, such as compound 8, may be achieved via reductive amination with, for example, triethyl orthoformate in TFA followed by treatment with NaBH$_4$ to give the corresponding secondary C3-amine derivative (such as N-methyl-C3-amino-quinoline 9). The secondary C3-amine derivative intermediate (e.g., compound 9) may then be methylated to obtain the desired cation (e.g., compound 1f).

In some embodiments, preparation of certain cations of the invention may occur via a one-pot procedure reported by Venkatesan et al. involving a SnCl₂ mediated Friedlander synthesis followed by Curtius rearrangement and deprotection with subsequent alkylation, as exemplified with the preparation of cation 2j (Scheme 3).

In particular, cation 2j may be prepared from 5-fluoro-2-nitro-benzaldehyde 11 via a one-pot procedure reported by Venkatesan et al. involving a SnCl₂ mediated Friedlander synthesis to construct the desired C2-ethyl-carboxylate quinoline 12 (Scheme 3). The resulting ester group may then be hydrolyzed and converted into acyl azide with DPPA, followed by Curtius rearrangement with an alcohol, such as tert-butanol, to provide the corresponding N-Boc protected substrate (not depicted). N-Boc deprotection with TFA provides the corresponding fluorinated C3-amino-quinoline intermediate 13. Methylation of precursor 13 may then occur using, for example, the general method outlined in Scheme 1 to obtain cation 2j.

e.g., mCPBA) followed by nitration and chlorination, respectively and further followed by amination and alkylation, respectively, as exemplified with the preparation of cation 2k (Scheme 4).

In particular, cation 2k may be prepared from quinoline-N-oxide 14 or the like, which may be derived from quinoline via a mCPBA oxidation (Scheme 4). A regioselective nitration of 14 may be used to selectively install a nitro group at the C3 position of compound 14 or the like, followed by chlorination of the quinoline-N-oxide moiety in the presence of POCl₃ to give intermediate 15. The desired C2/3-di-amino-group may be introduced via a two-step sequence involving an amination of C2-chloro- group with, for example, ammonia and reduction of C3-nitro group (via, e.g., hydrogenation) to give the precursor 16. Compound 16 may be methylated using, for example, the general method outlined in Scheme 1 to give cation 2k.

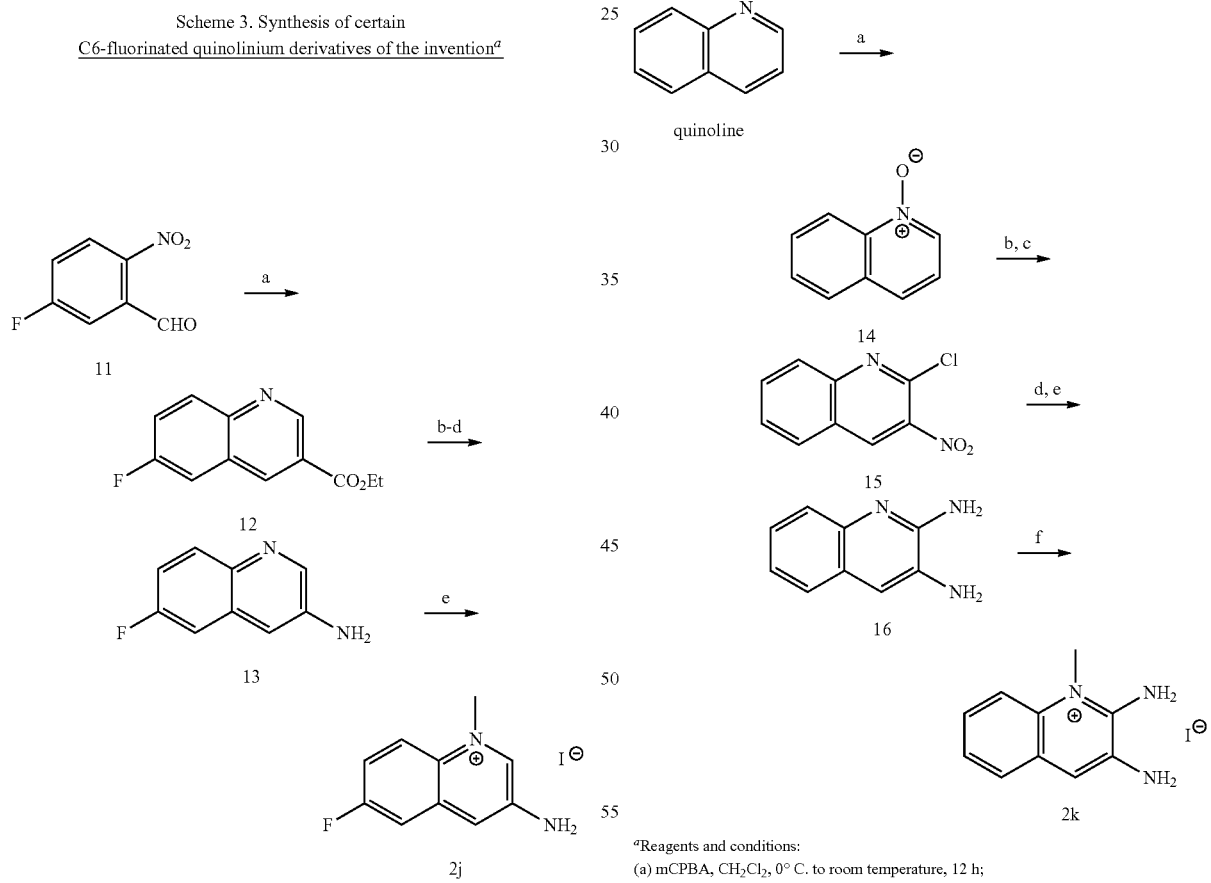

Scheme 3. Synthesis of certain C6-fluorinated quinolinium derivatives of the invention<sup>a</sup>

<sup>a</sup>Reagents and conditions:
(a) SnCl₂•2H₂O, ethyl 3,3-diethoxypropionate, EtOH, 90° C., 24 h
(b) 3N NaOH, MeOH, room temperature, 2 h;
(c) Diphenyl phosphoryl azide, Et₃N, toluene, room temperature, 30 min then tert-BuOH, reflux, 12 h;
(d) TFA/CH₂Cl₂, room temperature, 3 h,;
(e) MeI, IPA, 90° C., 12 h.

Scheme 4. Synthesis of certain C2,3-diamino-quinolinium derivatives of the invention<sup>a</sup>

<sup>a</sup>Reagents and conditions:
(a) mCPBA, CH₂Cl₂, 0° C. to room temperature, 12 h;
(b) tert-butyl nitrite, MeCN, 100° C., 24 h;
(c) POCl₃, 95° C., 12 h;
(d) NH₃ (7N in MeOH), 90° C., 12 h;
(e) Pd/C, H₂, MeOH/THF, room temperature, 12 h;
(f) MeI, IPA, 90° C., 12 h.

In some embodiments, preparation of certain cations of the invention may occur via oxidation of quinoline (using Use of NNMT Inhibitors to Provide Muscular Therapy Another aspect of the invention pertains generally to the use of the NNMT inhibitors to provide muscular therapy. NNMT has been linked to a number of diseases/conditions.

For example, it has been shown that NNMT activity plays a role in certain neurological diseases/conditions. The inventors surprisingly discovered that NNMT inhibitors may be used for muscular therapy, including treatment of certain muscular dystrophy diseases.

In some embodiments, the invention encompasses use of one or more NNMT inhibitors for muscular therapy comprising contacting one or more cells with one or more NNMT inhibitors. In other embodiments, the invention encompasses use of NNMT inhibitors for treating a muscular dystrophy disease comprising contacting one or more cells with one or more NNMT inhibitors.

In some embodiments, the invention encompasses a method of providing muscular therapy by administering a cation of Formula I, wherein:

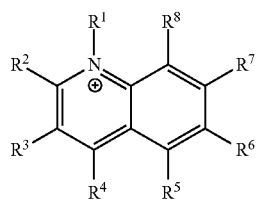

Formula I $R^1$ is $C_{1-4}$ alkyl;
$R^2$, $R^3$, $R^4$, and $R^5$ are independently selected from the group consisting of: H, C1-4 alkyl, halogen-substituted $C_{1-4}$ alkyl, $NR^9R^{10}$, and CN;
$R^6$ is H or halogen;
$R^7$ is H, methyl, or $NR^{11}R^{12}$; and
$R^8$ is H, $C_{1-4}$ alkyl, halogen-substituted $C_{1-4}$ alkyl;
$R^9$, $R^{10}$, $R^{11}$, and $R^{12}$ are independently selected from H and $C_{1-4}$ alkyl;
wherein the compound has at least two non-hydrogen substituents at positions $R^2$-$R^8$;
and wherein at least one of the non-hydrogen substituents at positions $R^2$-$R^8$ is $NH_2$.

In further embodiments, $R^1$ may be methyl or ethyl.
In further embodiments, $R^1$ is methyl.
In some embodiments, at least one of $R^2$ and $R^3$ is $NH_2$.
In some embodiments, $R^5$ is $NH_2$.
In some embodiments, $R^2$, $R^3$, and $R^4$ are hydrogen.
In some embodiments, $R^6$ is halogen.
In some embodiments, $R^6$ is F.
In some embodiments, $R^7$ is $NH_2$.
In some embodiments, $R^8$ is methyl or $CF_3$.
In some embodiments, $R^8$ is methyl.

In further embodiments, the invention encompasses a method of providing muscular therapy by administering a cation of Formula IA, wherein:

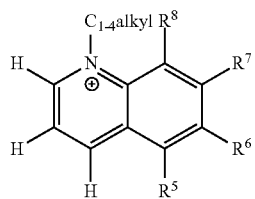

Formula IA the cation of Formula IA includes two or more non-hydrogen substituents at positions $R^2$-$R^8$, and wherein:

$R^5$ is H or $NH_2$,
$R^6$ is H or F;
$R^7$ is H or $NH_2$,
$R^8$ is H or methyl.

In some embodiments of Formula IA, $R^1$ is methyl or ethyl.

In some embodiments of Formula IA, $R^6$ is F.

In certain embodiments, the invention encompasses a method of providing muscular therapy by administering a cation of Formula IA, wherein said cation is chosen from:

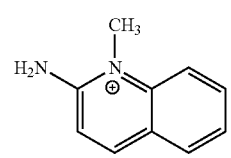

1c

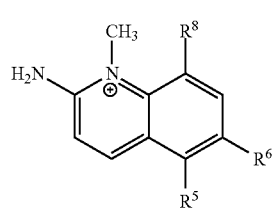

1c'

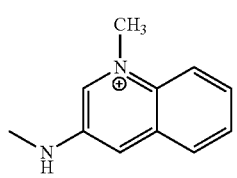

1f

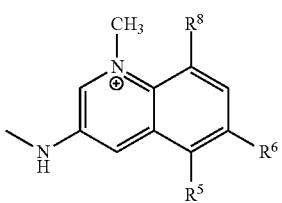

1f'

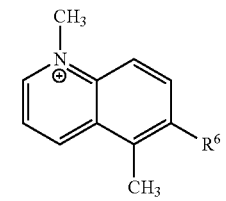

1l

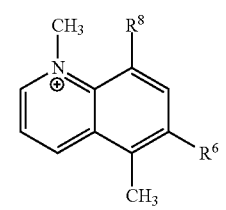

1l'

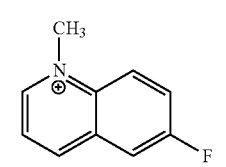

1m

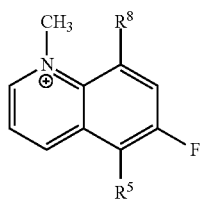
1m'

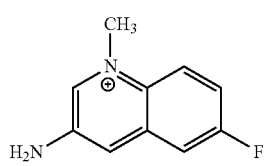
2j

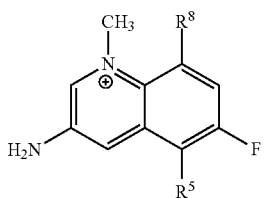
2j'

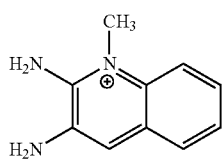
2m

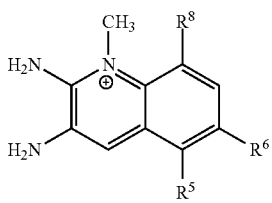
2m'

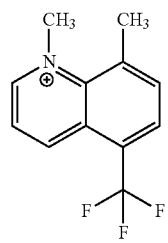
2k

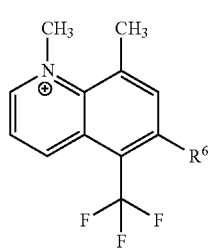
2k'

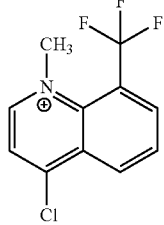
2l

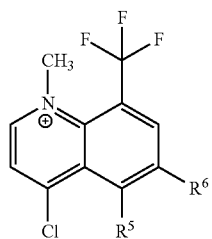
2l'

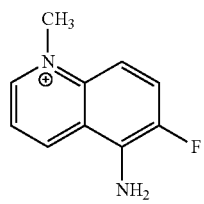
2aa

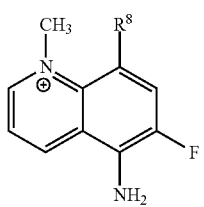
2aa' wherein:
$R^5$ is H or $NH_2$;
$R^6$ is H or F; and
$R^8$ is H or methyl.

In certain embodiments, the small molecule cations of described herein may be accompanied by a counter anion ($X^-$). In some embodiments, the counter ion may be chosen from sulfonate (e.g., trifluoromethanesulfonate, mesylate, tosylate, besylate, and the like); halide (e.g., fluoride, bromide, chloride or iodide); acetate; sulfate; bisulfate; nitrate; oxalate; valerate; oleate; palmitate; stearate; laurate; borate; benzoate; lactate; phosphate; citrate; maleate; fumarate; succinate; tartrate; glucoheptonate; and lactobionate.

In certain embodiments, the invention encompasses a method of providing muscular therapy by administering a cation of chosen from Tables 1, 2, 3a, and 3b, described herein.

In some embodiments, the invention encompasses a method of providing muscular therapy by contacting a cell expressing NNMT with one or more cations of the invention. In further embodiments, the invention encompasses a method of providing muscular therapy by contacting a cell expressing NNMT with one or more cations chosen from 1c, 1f, 1l, 2m, 2j, 2k, 2l, 2m, 2aa, 1c', 1f', 1l', 1m', 2j', 2k', 2l', 2m', and 2aa'.

In further embodiments, the invention encompasses a method of providing muscular therapy by contacting a cell expressing NNMT with one or more cations chosen from Tables 1, 2, 3a, and 3b. In further embodiments, the invention encompasses a method of providing muscular therapy by contacting a cell expressing NNMT with one or more cations of the invention and with one or more cations chosen from Tables 3a and 3b. In one aspect of the invention, one or more cations of the invention is contacted with a cell expressing NNMT concurrently with one or more cations chosen from Tables 3a and 3b. In another aspect of the invention, one or more cations of the invention is contacted with a cell expressing NNMT followed by contacting said cell expressing NNMT with one or more cations chosen from Tables 3a and 3b. In a further aspect of the invention, one or more cations chosen from Tables 3a and 3b is contacted with a cell expressing NNMT followed by contacting said cell expressing NNMT with one or more cations of the invention.

In some embodiments, the invention encompasses a method of providing muscular therapy by administering a therapeutically effective amount of one or more NNMT inhibitors. In some embodiments, the invention encompasses a method of providing muscular therapy by administering a therapeutically effective amount of one or more cations of the invention. Another aspect of the invention pertains to a method of providing muscular therapy by administering a therapeutically effective amount of one or more cations.

In further embodiments, the invention encompasses a method of providing muscular therapy by administering a therapeutically effective amount of one or more cations chosen from 1c, 1f, 1l, 1m, 2j, 2k, 2l, 2m, 2aa, 1c', 1f', 1l', 1m', 2j', 2k', 2l', 2m', and 2aa'.

In further embodiments, the invention encompasses a providing muscular therapy by administering a therapeutically effective amount of one or more cations chosen from Tables 1, 2, 3a, and 3b. In further embodiments, the invention encompasses a method of providing muscular therapy by administering a therapeutically effective amount of one or more cations of the invention and one or more cations chosen from Tables 3a and 3b. One aspect of the invention pertains to treating providing muscular therapy by administering a therapeutically effective amount of one or more cations of the invention with concurrent administration of one or more cations chosen from Tables 3a and 3b. Another aspect of the invention pertains to providing muscular therapy by administering a therapeutically effective amount of one or more cations of the invention followed by administration of one or more cations chosen from Tables 3a and 3b. A further aspect of the invention pertains to providing muscular therapy by administering a therapeutically effective amount of one or more cations chosen from Tables 3a and 3b followed by the administration of one or more cations of the invention.

One aspect of the invention pertains to the administration of one or more NNMT inhibitors by, for example, contacting one or more cells of an animal to:
  (a) treat and/or prevent muscular disorders, including, but not limited to, sarcopenia, muscle atrophy, Duchenne muscular dystrophy, Becker muscular dystrophy, Limb-girdle muscular dystrophies, Pompe disease, cardiac myopathies, pulmonary disorders;
  (b) improve neuromuscular function, including, but not limited to, following acute muscle injury, following overuse muscle injury, following chronic muscle injury, during strength/resistance and/or endurance training, during/following muscle dysfunction accompanying aging, following muscular atrophy;
  (c) reduce the time required to restore neuromuscular function, including, but not limited to, following acute muscle injury, following overuse muscle injury, and/or following chronic muscle injury;
  (d) prevent neuromuscular injury, including, but not limited to, associated with activities that may produce acute, overuse, and/or chronic muscle injury; and
  (e) improve muscle regeneration.

In further embodiments, administration of the NNMT inhibitor is in vitro. In further embodiments, administration of the NNMT inhibitor is in vivo.

In some embodiments, NNMT inhibitors may be used with one or more chemical entities (e.g., nicotinamide riboside, nicotinamide mononucleotide) that increase intracellular NAD+ levels, to produce synergistic or additive effects to provide muscular therapy.

In some embodiments, the invention encompasses a method of providing muscular therapy by co-administering a therapeutically effective amount of one or more NNMT inhibitors with one or more chemical entities (e.g., nicotinamide riboside, nicotinamide mononucleotide) that increase intracellular NAD+ levels to provide muscular therapy.

In further embodiments, the invention encompasses a method of providing muscular therapy by contacting a cell expressing NNMT with a NNMT inhibitor (such as a cation of Formula I or IA, or otherwise disclosed herein) and one or more chemical entities (e.g., nicotinamide riboside, nicotinamide mononucleotide) that modulates intracellular NAD+ levels to provide muscular therapy. In some embodiments, the invention encompasses a method of providing muscular therapy by contacting a cell expressing NNMT with a NNMT inhibitor (such as a cation of Formula I or IA, or otherwise disclosed herein) and one or more chemical entities (e.g., nicotinamide riboside, nicotinamide mononucleotide) that increases intracellular NAD+ levels to provide muscular therapy.

In one aspect of the invention, one or more NNMT inhibitors (such as a cation of Formula I or IA, or otherwise disclosed herein) is contacted with a cell expressing NNMT concurrently with one or more chemical entities (e.g., nicotinamide riboside, nicotinamide mononucleotide) that increase intracellular NAD+ levels to provide muscular therapy. In some embodiments, the invention encompasses contacting one or more NNMT inhibitors (such as a cation of Formula I or IA, or otherwise disclosed herein) is contacted with a cell expressing NNMT concurrently with one or more chemical entities (e.g., nicotinamide riboside, nicotinamide mononucleotide) that modulate intracellular NAD+ levels to provide muscular therapy.

In another aspect of the invention, one or more NNMT inhibitors (such as a cation of Formula I or IA, or otherwise disclosed herein) is contacted with a cell expressing NNMT followed by contacting said cell expressing NNMT with one or more chemical entities (e.g., nicotinamide riboside, nicotinamide mononucleotide) that modulate intracellular NAD+ levels to provide muscular therapy.

In another aspect of the invention, one or more NNMT inhibitors (such as a cation of Formula I or IA, or otherwise disclosed herein) is contacted with a cell expressing NNMT followed by contacting said cell expressing NNMT with one or more chemical entities (e.g., nicotinamide riboside, nicotinamide mononucleotide) that increase intracellular NAD+ levels to provide muscular therapy.

In a further aspect of the invention, one or more chemical entities (e.g., nicotinamide riboside, nicotinamide mononucleotide) that modulate intracellular NAD+ levels to provide muscular therapy is contacted with a cell expressing NNMT followed by contacting said cell expressing NNMT one or more NNMT inhibitors (such as a cation of Formula I or IA, or otherwise disclosed herein).

In a further aspect of the invention, one or more chemical entities (e.g., nicotinamide riboside, nicotinamide mononucleotide) that increase intracellular NAD+ levels to provide muscular therapy is contacted with a cell expressing NNMT followed by contacting said cell expressing NNMT one or more NNMT inhibitors (such as a cation of Formula I or IA, or otherwise disclosed herein).

EXAMPLES

Example 1. Preparation of Certain Exemplary Embodiments of the Invention

Chemistry. The identity of all the tested compounds was confirmed by 1H NMR and HPLC-MS, and the purity was ensured to be ≥95% (see Supporting Information).

SAM was obtained from Sigma Aldrich and nicotinamide from Fluka Analytical (Kwazulu Natal, South Africa; distributed by Sigma Aldrich in the USA). MNA chloride and S-adenosylhomocysteine (SAH) were obtained from Cayman Chemical Company (Ann Arbor, MI). All compounds were made in double distilled water.

General procedures. Unless otherwise indicated all reactions were conducted in standard commercially available glassware using standard synthetic chemistry methods and setup. All air- and moisture-sensitive reactions were performed under nitrogen atmosphere with dried solvents and glassware under anhydrous conditions. Starting materials and reagents were commercial compounds of the highest purity available and were used without purification. Solvents used for reactions were indicated as of commercial dry or extra-dry or analytical grade. Analytical thin layer chromatography was performed on aluminium plates coated with Merck Kieselgel 60F254 and visualized by UV irradiation (254 nm) or by staining with a solution of potassium permanganate.

Flash column chromatography was performed on Biotage Isolera One 2.2 using commercial columns that were prepacked with Merck Kieselgel 60 (230-400 mesh) silica gel. Compounds for biological testing were all ≥95% purity as determined by HPLC-MS and 1H NMR.

NMR. NMR experiments were recorded on Agilent DD2 400 MHz spectrometers at ambient temperature. Samples were dissolved and prepared in deuterated solvents (CDCl$_3$, CD$_3$OD and DMSOd$_6$) with residual solvents being used as the internal standard in all cases. All deuterated solvent peaks were corrected to the standard chemical shifts (CDCl$_3$, d$_H$=7.26 ppm; CD$_3$OD, d$_H$=3.31 ppm; DMSO-d$_6$, d$_H$=2.50 ppm). Spectra were all manually integrated after automatic baseline correction. Chemical shifts (d) are given in parts per million (ppm), and coupling constants (J) are given in Hertz (Hz).

The proton spectra are reported as follows: d (multiplicity, coupling constant J, number of protons). The following abbreviations were used to explain the multiplicities: app=apparent, b=broad, d=doublet, dd=doublet of doublets, ddd=doublet of doublet of doublets, dddd=doublet of doublet of doublet of doublets, m=multiplet, s=singlet, t=triplet.

HPLC-MS. All samples were analyzed on Agilent 1290 series HPLC system comprised of binary pumps, degasser and UV detector, equipped with an auto-sampler that is coupled with Agilent 6150 mass spectrometer. Purity was determined via UV detection with a bandwidth of 170 nm in the range from 230-400 nm. The general LC parameters were as follows: Column—Zorbax Eclipse Plus C18, size 2.1×50 mm; Solvent A: 0.10% formic acid in water, Solvent B: 0.00% formic acid in acetonitrile; Flow rate-0.7 mL/min; Gradient: 5% B to 95% B in 5 min and hold at 95% B for 2 min; UV detector—channel 1=254 nm, channel 2=254 nm. Mass detector AJS-ES.

Synthesis—General Procedure A: quinolinyl ring N-alkylation using methyl iodide (MeI)

A mixture of appropriate quinoline derivative (approximately 1 equiv.) and MeI (approximately 1.5 equiv unless otherwise indicated) in 0.5M isopropyl alcohol (IPA) was heated at 90° C. for approximately 12 h. The reaction was cooled to ambient temperature and the resulting precipitate was isolated by vacuum filtration, washed with a mixture of IPA/Et$_2$O (v:v/1:1), and dried in vacuo.

Synthesis—General Procedure B: quinolinyl ring N-alkylation using MeOTf

A mixture of appropriate quinoline derivative (approximately 1 equiv) and methyl trifluoromethansulfonate (MeOTf) (approximately 3 equiv, unless otherwise indicated) in toluene (0.2M) was heated at 100° C. for 12 h. The reaction was cooled to ambient temperature and added Et$_2$O to induce precipitation. The resulting precipitate was isolated by vacuum filtration, washed with Et$_2$O, and dried in vacuo.

Preparation of Certain Exemplary Embodiments of the Invention 2-amino-1-methylquinolin-1-ium iodide (1c)

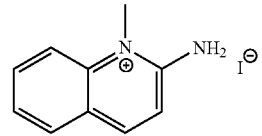

According to general procedure A, the title compound was obtained as grey powder (26% yield). $^1$H NMR (400 MHz, DMSO-d$_6$) δ 9.45 (br, 1H), 8.87 (br, 1H), 8.34 (d, J=9.2 Hz, 1H), 8.01 (d, J=8.8 Hz, 1H), 7.98 (d, J=8.8 Hz, 1H), 7.87 (dd, J=8.4, 7.6 Hz, 1H), 7.57 (dd, J=7.6, 7.6 Hz, 1H), 7.17 (d, J=9.2 Hz, 1H), 3.87 (s, 3H). HPLC-MS (AJS-ES): Rt 1.31 min, m/z 159.1 [M+−I].

1-methyl-3-(methylamino)quinolin-1-ium iodide (1f)

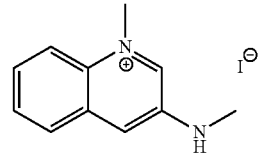

According to general procedure A, the title compound was obtained as orange powder (72% yield). $^1$H NMR (400

MHz, DMSO-$d_6$) δ 8.90 (d, J=2.4 Hz, 1H), 8.22 (dd, J=4.8, 4.4 Hz, 1H), 8.10 (dd, J=4.8, 4.4 Hz, 1H), 7.97 (d, J=1.6 Hz, 1H), 7.78 (dd, J=4.8, 4.4 Hz, 1H), 7.13 (br, 1H), 4.54 (s, 3H), 2.90 (s, 3H); HPLC-MS (AJS-ES): Rt 0.78 min, m/z 173.1 [M+−I].

6-amino-1-methylquinolin-1-ium iodide (1m)

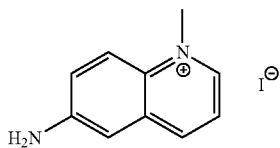

According to general procedure A, the title compound was obtained as orange-brown powder (58% yield). $^1$H NMR (400 MHz, DMSO-$d_6$) δ 8.94 (s, 1H), 8.77 (d, J=9.2 Hz, 1H), 8.18 (d, J=9.2 Hz, 1H), 7.83 (m, 1H), 7.58 (d, J=9.2 Hz, 1H), 7.11 (s, 1H), 6.46 (br, 2H), 4.48 (s, 3H); HPLC-MS (AJS-ES): Rt 0.74 min, m/z 159.1 [M+−I].

3-amino-6-fluoro-1-methylquinolin-1-ium (2j)

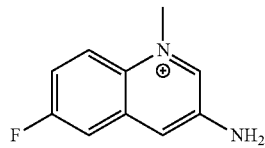

According to general procedure A, the title compound was obtained as yellow powder (58% yield). $^1$H NMR (400 MHz, DMSO-$d_6$) δ 8.84 (d, J=2.0 Hz, 1H), 8.35 (dd, J=9.6, 4.4 Hz, 1H), 7.99 (dd, J=9.2, 2.8 Hz, 1H), 7.94 (d, J=2.0 Hz, 1H), 7.76 (ddd, J=8.8, 8.8, 3.2 Hz, 1H), 6.78 (br, 2H), 4.56 (s, 3H); HPLC-MS (AJS-ES): Rt 0.22 min, m/z 177.1 [M+−I].

4-chloro-1-methyl-8-(trifluoromethyl)quinolin-1-ium trifluoromethanesulfonate (2l)

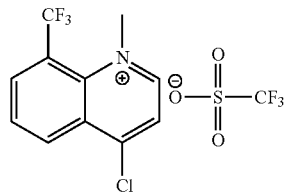 [SMILES: C[n+]1ccc(Cl)c2cccc(C(F)(F)F)c21 ; O=S(=O)([O-])C(F)(F)F]

According to general procedure B, the title compound was obtained using excess amount of MeOTf (5 equiv) to isolate the product as pale grey powder (88% yield). $^1$H NMR (400 MHz, DMSO-$d_6$) δ 8.56 (m, 1H), 8.33-8.10 (m, 2H), 7.59 (m, 1H), 6.47 (m, 1H), 3.93 (m, 3H); HPLC-MS (AJS-ES): Rt 0.92 min, m/z 226.1 [M+—OSO$_2$CF$_3$].

Biology. Expression and Purification of Recombinant hNNMT. A modified mutant human NNMT (mt-hNNMT) [lacking 3 amino acid residues from the C-terminus of the NNMT protein that was not observed in crystal structure] (3ROD, PDB accession code) cloned into an IPTG-inducible plasmid pJ401 expression vector was purchased from DNA 2.0 (Menlo Park, CA). The expression and purification of mt-hNNMT was modified from a previously reported protocol. Briefly, the expression vector was used to transform chemically competent E. coli BL21/DE3 cells. The BL21 transformants were plated on LB agar plate with kanamycin (KAN) (30 µg/mL) and incubated overnight at 37° C. that was used to inoculate 1 L media along with 0.5 mM each of magnesium and calcium chloride for protein over-expression.

The culture was placed in a shaker at 37° C. to an OD$_{600}$ of 0.7-0.8 (~2-3 h) before induction with 0.5 mM IPTG and incubated for an additional 3 h. Cells were harvested by centrifugation at 10° C. and 4000 rpm for 20 min and removal of the supernatant. For purification, harvested cells were first re-suspended in chilled lysis buffer (20 mM Tris [pH 7.9], 0.5 M NaCl, 5 mM imidazole, 10% glycerol, 1 mM DTT, 1 mM PMSF) and the lysis mixture was sonicated on ice. Cell lysates were centrifuged at 4° C. and 15000 rpm for 30 min. The soluble fraction was loaded onto a nickel affinity column formed from nickel sepharose beads (GE Biosciences) pre-equilibrated with lysis buffer.

The column was washed with lysis buffer (5 mM imidazole in lysis buffer) and increasing concentrations of NaCl (0.5 mM and 1 mM) followed by increasing concentrations of imidazole (5 mM and 20 mM, in lysis buffer) to remove contaminating proteins. Bound mt-hNNMT was eluted from the column with lysis buffer and 150 mM imidazole, 200 mM salt, and 5% glycerol in 1 ml aliquots. Collected fractions were run on SDS-PAGE to verify protein expression and dialyzed into storage buffer (25 mM Tris [pH 8.6], 20% glycerol, 100 mM NaCl, 1 mM DTT). Pooled protein dialysate concentration was determined by UV spectroscopy, portioned into 120 uL aliquots with 20% final glycerol concentration, flash-frozen in liquid nitrogen, and stored at −70° C.

NNMT Activity Assay: HPLC Instrumentation and Chromatographic Conditions. An HPLC-UV method for the detection of NNMT catalyzed product, 1-methyl nicotinamide (MNA) was developed by modifying a previously reported protocol (Patel et al. 2013). Shimatzu 10AVP HPLC System (Shimatzu, Kyoto, Japan) with manual sample injector was used to run the HPLC-UV method on an isocratic gradient with mobile phase comprising of 10 mM 1-heptane sulfonate, 20 mM potassium phosphate monobasic [pH 3.1], 4% methanol, and 3% acetonitrile. Chromatographic separation was achieved on a Platinum EPS C18 100A 3u (length: 53 mm, internal diameter: 7 mm, maximum pressure: 5000 PSIG) analytical column (Alltech Associates, Inc., Deerfield, IL) at ambient temperature with a flow rate of the mobile phase maintained at 1 ml/min. Sample injection volume was 100 µL with a run time of 20 min per sample.

MNA Calibration Curve and NNMT Activity Assay. To establish a linear curve for the detection of MNA peak, a 10-0.3125 uM/100 µL half-fold serially diluted samples of MNA were prepared in reaction buffer containing 1 mM Tris [pH 8.6], 1 mM DTT, 10% trichloroacetic acid, 4% methanol, and water. Similarly, substrate nicotinamide at 100 µM, methyl donor S-adenosyl-L-methionine (SAM) at 5 µM, and S-adenosyl methionine (SAH) at 5 µM concentration) samples were also run individually in the reaction buffer [1 mM Tris [pH 8.6], 1 mM DTT, 10% trichloroacetic acid, 4% methanol, and water] to identify elution time and define substrate, co-factor, and product peaks. MNA, nicotinamide, SAM, and SAH peaks were detected using a wavelength of 265 nm. To determine NNMT activity, 5 μL of 10 mM nicotinamide made in water, 2.5 μL of 1 mM SAM made in water were added/500 μL of the reaction buffer. The reaction was initiated by adding 4 μL of 25 μM stock purified NNMT protein (final concentration of NNMT in the reaction was 200 nM) and incubated on a heat block at 37° C. for 6 min, following which the reaction was terminated by the addition of a mixture of 10% trichloroacetic acid and 4% methanol, vortexing for 5 s, and centrifuging at 14,000 rpm for 2 min to precipitate the protein. Peak area and peak height for MNA were determined by running 100 μL of the supernatant using the chromatographic conditions described above. Reactions were run in the absence of NNMT as control samples in each experiment.

NNMT $IC_{50}$ Curves for Inhibitors. NNMT reaction products were analyzed by HPLC as described above, and used to construct inhibition curves for 1-MQ and 1-MQ analogs. Compounds were initially tested for NNMT inhibition activity at 100 μM or 1 mM concentration (compounds with no activity at 100 uM were tested at 1 mM concentration). Compounds with >50% inhibitory activity at 1 mM were advanced to comprehensive concentration-response analysis (concentration range of 100 nM-1 mM/100 μL reaction). Otherwise, $IC_{50}$ values are reported as either >1000 uM or no observable inhibition (NI). Data were normalized and reported as % NNMT activity against concentrations tested (uM). $IC_{50}$ values were determined by three parameters non-linear regression [inhibitor conc. vs. normalized % NNMT activity] fitted by least squares method (Graphpad Prism 7.0, GraphPad Software Inc., La Jolla, CA). For compounds with IC50 values lower than 20 μM and/or R2 values for the curve fit <0.8, data sets were run in duplicates or triplicates and averaged for analyses.

Molecular Docking. Certain embodiments of the invention (and certain structural analogs) were virtually docked to NCA binding site of the mt-hNNMT monomer chain A [3ROD, PDB accession code] using the AutoDock Vina program. Analog conformations with the lowest negative Vina docking scores represented the predicted bound inhibitor conformation with most favorable interactions within the NCA active site of the NNMT protein. A correlation analysis using Pearson's correlation was performed between the Vina docking scores and experimentally established IC50 for the respective compounds (Graphpad Prism 7.0, GraphPad Software Inc., La Jolla, CA).

Docked output PDB files generated from the Vina docking for the analogs with the lowest IC50 value within each scaffold with the hNNMT monomer (3ROD, PDB accession code) were used to generate docked image using the Auto Dock Tools (ADT) molecular graphics program. Docked PDB files for the ligands and hNNMT monomer (3ROD, PDB accession code) were also used in LigPlot+ program (Wallace et al., 1995) to generate representative two-dimensional images indicating hydrogen bonds and hydrophobic interactions within 4 Å distance between key catalytic residues in the NCA active site of the NNMT and the inhibitor analogs. NCA substrate site in NNMT/inhibitor contact diagrams were used to describe and develop the initial SAR parameters for this system.

Example 2. Biological Evaluation of Certain Embodiments of the Invention (and Analogs Thereof)

The ability of cations of the invention to inhibit NNMT was investigated by probing the inhibitory activity of cations listed in Tables 1 and 2, below. The inventors surprisingly found that cations 1c, 1f, 1l, and 1m exhibited inhibitory activity against NNMT.

TABLE 1

NNMT inhibitory activities of certain exemplary embodiments of the invention with single positional substitutions when R1 is methyl Formula I

| Exemplary Embodiment of the Invention | R1 | R2 | R3 | R4 | R5 | R6 | R7 | R8 | NNMT Inhibition $IC_{50}$ (uM)[a] |
|---|---|---|---|---|---|---|---|---|---|
| 1c | $CH_3$ | $NH_2$ | H | H | H | H | H | H | 6.3 ± 1.1[b] |
| 1f | $CH_3$ | H | $NHCH_3$ | H | H | H | H | H | 4.0 ± 1.5[b] |
| 1l | $CH_3$ | H | H | H | H | $CH_3$ | H | H | 13.1 ± 5.1[b] |
| 1m | $CH_3$ | H | H | H | H | $NH_2$ | H | H | 34.4 ± 9.6[b] |

[a]$IC_{50}$ values are represented at mean ± SD of duplicate or triplicate measurements.

The inventors also surprisingly found inhibitory activity with certain embodiments of the invention where $R^1$ is methyl with dual positional substitutions (see e.g., compounds 2j, 2m, 2k, and 2l, Table 2).

TABLE 2

NNMT inhibitory activities of certain exemplary embodiments of the invention with dual positional substitutions when R1 is methyl Formula I

| Exemplary Embodiment of the Invention | R1 | R2 | R3 | R4 | R5 | R6 | R7 | R8 | NNMT Inhibition $IC_{50}$ (uM)[a] |
|---|---|---|---|---|---|---|---|---|---|
| 2j | $CH_3$ | H | $NH_2$ | H | H | F | H | H | 1.2 ± 0.2[b] |
| 2k | $CH_3$ | H | H | H | $CF_3$ | H | H | $CH_3$ | 87.01 ± 26.1[b] |
| 2l | $CH_3$ | H | H | Cl | H | H | H | $CF_3$ | >1000[b] |
| 2m | $CH_3$ | $NH_2$ | $NH_2$ | H | H | H | H | H | 2.8 ± 0.5[b] |

[a]$IC_{50}$ values are represented at mean ± SD of duplicate or triplicate measurements.

The inventors have also surprisingly discovered that certain analogs of the invention have the ability to inhibit NNMT (see Table 3).

TABLE 3a

Analogs of Certain Embodiments of the Invention with NNMT Inhibitory Activity

| Cpd. | R1 | R2 | R3 | R4 | R5 | R6 | R7 | R8 | NNMT Inhibition IC$_{50}$ (uM)[a] |
|---|---|---|---|---|---|---|---|---|---|
| 1a (1-MQ) | CH$_3$ | H | H | H | H | H | H | H | 12.1 ± 3.1 |
| 1b | CH$_3$ | CH$_3$ | H | H | H | H | H | H | 21.03 ± 2.1[b] |
| 1d | CH$_3$ | H | NH$_2$ | H | H | H | H | H | 2.9 ± 0.7[b] |
| 1e | CH$_3$ | H | CN | H | H | H | H | H | 23.8 ± 5.6 |
| 1g | CH$_3$ | H | NHPh | H | H | H | H | H | >1000[b] |
| 1h | CH$_3$ | H | H | CH$_3$ | H | H | H | H | 7.5 ± 2.2 |
| 1i | CH$_3$ | H | H | NH$_2$ | H | H | H | H | 11.4 ± 2.1[b] |
| 1j | CH$_3$ | H | H | H | NH$_2$ | H | H | H | 1.2 ± 0.1[b] |
| 1k | CH$_3$ | H | H | H | H | F | H | H | 5.7 ± 1.8[b] |
| 1n | CH$_3$ | H | H | H | H | OCH$_3$ | H | H | 119.9 ± 50.1 |
| 1o | CH$_3$ | H | H | H | H | H | NH$_2$ | H | 2.6 ± 0.5[b] |
| 1p | CH$_3$ | H | H | H | H | H | OH | H | 709.2 ± 178.9 |
| 1q | CH$_3$ | H | H | H | H | H | H | CH$_3$ | 1.8 ± 0.5 |
| 1r | CH$_3$ | H | H | H | H | H | H | OH | 95.2 ± 21.02 |
| 1s | CH$_3$ | H | H | H | H | H | H | H | 27.1 ± 5.4 |
| 1t | —CH$_2$CH$_2$CH$_2$OCH$_3$ | H | H | H | H | H | H | H | >1000 |
| 1u | —CH$_2$C(O)Ph | H | H | H | H | H | H | H | >1000 |
| 1v | —CH(CH$_3$)C(O)-C$_6$H$_4$-Br (4-bromobenzoyl) | H | H | H | H | H | H | H | >1000 |
| 1w | N-alkyl chlorocyclohexene dicarboximide | H | H | H | H | H | H | H | >1000 |

[a]IC$_{50}$ values are represented at mean±SD of duplicate or triplicate measurements.

TABLE 3b

Analogs of Certain Embodiments of the Invention with NNMT Inhibitory Activity

[Structure: quinolinium core with substituents R1 on N1+, R2, R3, R4, R5, R6, R7, R8]

| Cpd. | R1 | R2 | R3 | R4 | R5 | R6 | R7 | R8 | NNMT Inhibition IC$_{50}$ (uM)$^a$ |
|---|---|---|---|---|---|---|---|---|---|
| 2a | CH$_2$CH$_3$ | H | H | CH$_3$ | H | H | H | H | 8.7 ± 2.6 |
| 2b | CH$_2$CH$_3$ | H | H | H | H | H | H | CH$_3$ | 3.1 ± 1.4 |
| 2c | -CH$_2$CH$_2$OH | H | H | CH$_3$ | H | H | H | H | 33.5 ± 9.9 |
| 2d | -CH$_2$C(O)CH$_3$ | H | H | H | H | H | H | OH | 40.6 ± 13.01 |
| 2e | -CH$_2$CH(OH)CH$_2$Br | H | Br | H | H | H | H | H | >1000 |
| 2f | CH$_2$CH$_2$CH$_3$ | H | H | H | H | CH$_3$ | H | H | >1000 |
| 2g | -CH$_2$C(O)CH$_3$ | H | H | H | H | Cl | H | H | >1000 |
| 2h | -CH$_2$C(O)CH$_3$ | H | H | H | H | OH | H | H | >1000 |
| 2i | -CH$_2$C(O)C$_6$H$_5$ | H | H | H | H | CH$_3$ | H | H | NI |
| 2n | CH$_3$ | CH$_3$ | H | H | H | CH$_3$ | H | H | >1000$^b$ |

$^a$IC$_{50}$ values are represented at mean±SD of duplicate or triplicate measurements.

Example 3. Molecular Docking and Binding Modes of Inhibitors

Figure 2:
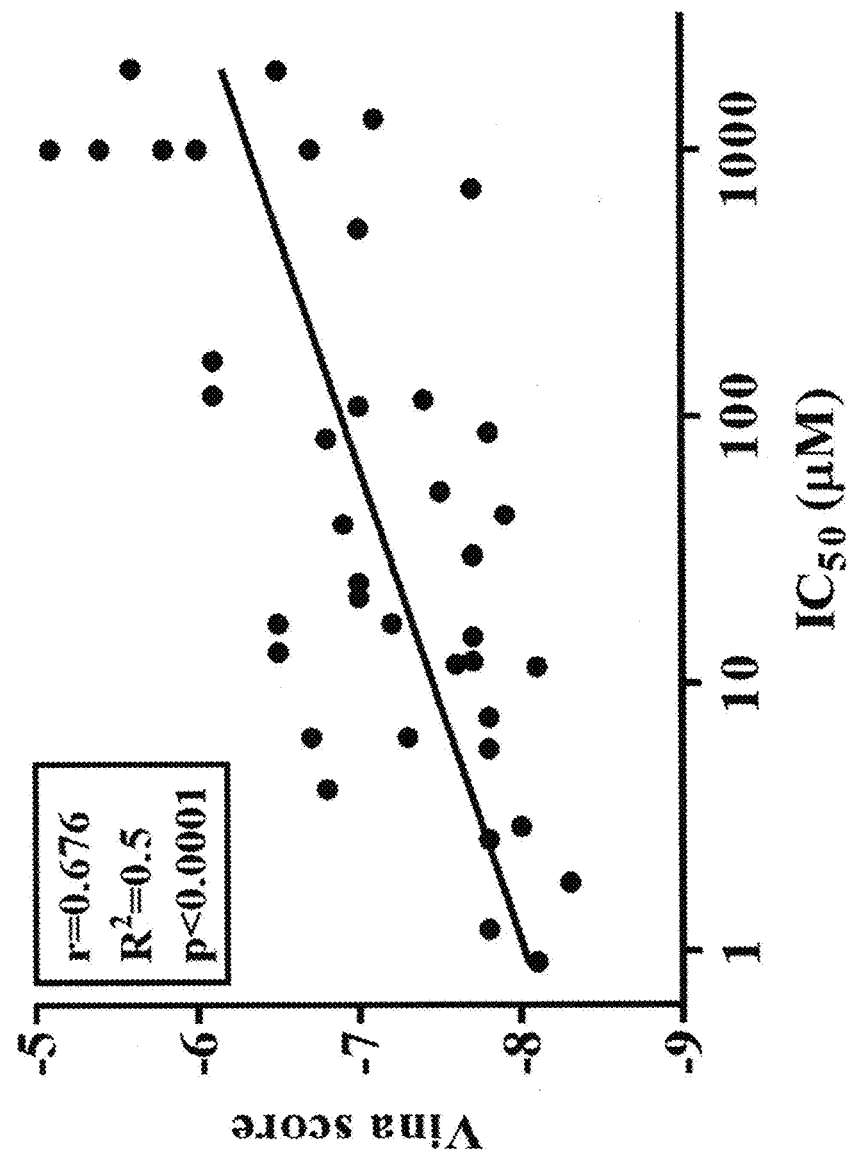
FIG. 2. Correlation between the Vina docking scores determined using AutoDock Vina Program and experimentally established $IC_{50}$ values for all analogs with methyl substitution at the N1'-position in each of the core scaffolds (~40 compounds). Pearson's correlation analysis indicated a modest positive linear correlation between calculated docking score (indicative of energetic interactions between the analog and the NNMT active site) and inhibitor potency ($IC_{50}$ value) (r=0.676, p<0.0001, R2=0.5).

A correlation analysis using Pearson's correlation between the Vina docking scores and experimentally established IC$_{50}$ values for certain embodiments of the invention indicated a modest positive linear correlation (see FIG. 2, r=0.676, p<0.0001, R$^2$=0.5). Some of the tested compounds with the most negative docking scores (i.e., lowest dockings scores; e.g., compound 1j, docking score=−8.1), is indicative of more energetic interactions with the target NNMT enzyme, exhibited high potency (i.e., 1j, IC$_{50}$=1.2 μM) and vice-versa (all compounds with docking scores between −6.0 and −5.0 had IC$_{50}$>1000 μM).

It has been found that the Vina docking calculations are useful to predict the binding modes, orientations, and conformations of small molecule inhibitors within the catalytic domain of the target protein.

Since the Vina docking calculations predict the binding modes, orientations, and conformations of small molecule inhibitors within the catalytic domain of the target protein, the docked output for the 1-MQ analog 1j with an IC$_{50}$ value of 1.2 μM was used to generate the predicted inhibitor-binding mode of 1j using the Auto Dock Tools (ADT) molecular graphics program. The predicted inhibitor-binding mode of 1j with an orientation and conformation that favors most negative docking score when superimposed with the endogenous substrate NCA of the NNMT enzyme indicated that the analog binds consistent with the binding mode of NCA, i.e., the N1-atom of both ligands aligned almost identical, conferring similar molecular interactions with key residues within the active site of the enzyme.

Figure 3:
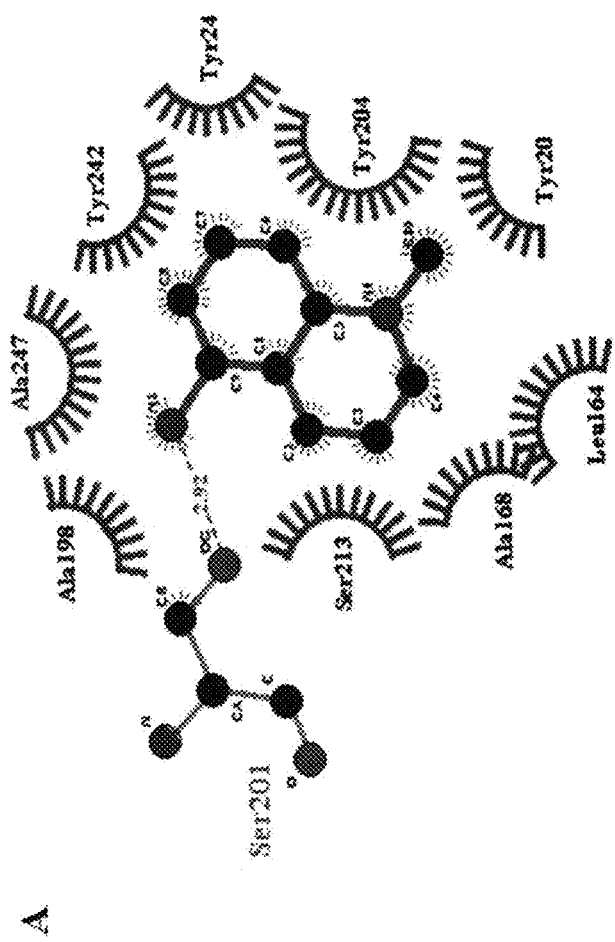
FIG. 3. Schematic of the NNMT active substrate-binding site with substrates (A) 5-amino-1-methylquinolinium (1j). Ligand interacting hydrophobic NNMT residues labels are red. Ligand interacting hydrogen bonding NNMT residue bonds are brown; residue/bonding distance labels are green. Schematics were produced with LIGPLOT.
Figure 4:
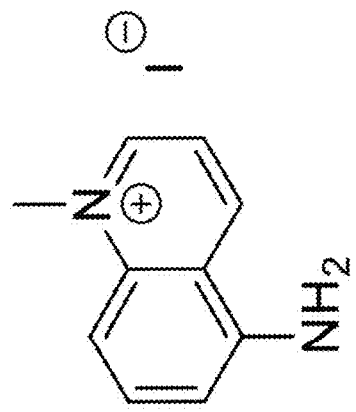
FIG. 4. The chemical structure of 5-amino-1-methylquinolin-1-ium iodide (1j)

The binding mode for 1j permits the formation of strong hydrophobic interactions within the apolar pocket surrounding the quinolinium N1-atom, consisting of Tyr20, Tyr204, Tyr242, Leu164, Ala198, and Ala247 residues (hydrophobic residues highlighted by red hashed lines, FIG. 3) that is consistent with the previous report on NCA pyridine ring binding to the active site of NNMT. The predicted binding mode of 1j indicates the $C_5'$-amino substituent forms hydrogen bonding interaction with the carboxylic backbone of the Ser201 residue and a hydrophobic bonding with the Ser213 residue unlike the NCA amide group that is in hydrogen bonding distance from with the NNMT Ser213 residue. These interactions for 1j might promote tighter binding affinity compared to the endogenous substrate NCA, further indicated by a much lower calculated Vina docking score for 1j (−8.1 vs for NCA) that suggests improved energetic interactions for 1j in the NNMT active site.

Figure 5:
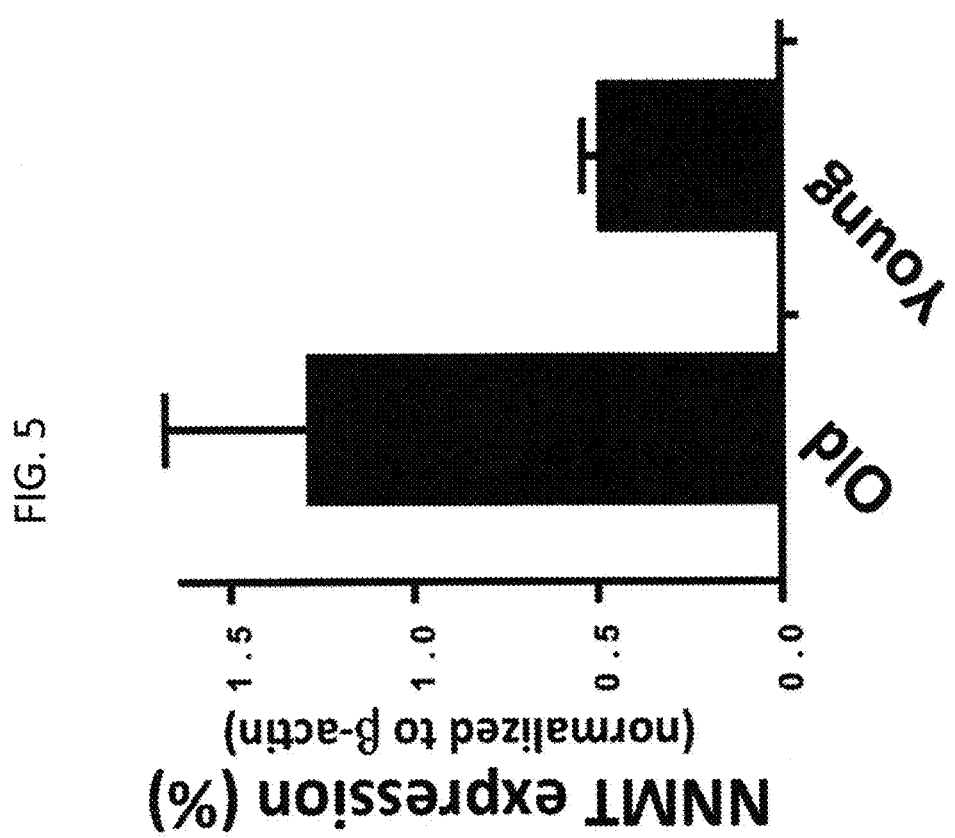
FIG. 5. Expression of NNMT protein (relative to β-actin) in tibealis anterior muscle isolated from old (27-mo C57BL6) and young (3-mo C57BL/6) mice (n=2). Expression levels quantitated from Western blotting using primary antibodies specific for either NNMT or β-actin.

Example 4. It has been observed that NNMT protein expression in muscle tissue was significantly greater in aged (27-mo old C57BL/6 mice) compared to young (3-mo old C57BL/6 mice) individuals (FIG. 5). Thus, NNMT inhibitors should reduce NNMT activity in aged muscles such that the NAD+ salvage cycle in aged muscle cells is returned to the functioning observed in young muscle cells.

Example 5. Small molecule NNMT inhibitors as highly membrane-permeable, selective inhibitors, which reduce intracellular 1-MNA levels and prevent lipogenesis in vitro were investigated. Furthermore, a proof-of-concept in vivo study in diet-induced obese mice to test the hypothesis that the most potent inhibitor when administered systemically, would reverse obesity by causing substantial loss of body weight and adiposity without causing any observable adverse effects was conducted.

Materials and Methods

Chemicals. NNMT inhibitors and standards for LC/MS/MS studies were purchased from established commercial suppliers or synthesized in-house by established synthetic schemes as described previously. SAM, NA, 1-MQ, 1,8-diMQ, NAD+, and 6-chloro nicotinamide (6-CN) were obtained from Sigma-Aldrich (St. Louis, MO, USA). 1-MNA and S-(5'-adenosyl)-L-methionine (SAH) were obtained from Cayman Chemical Company (Ann Arbor, MI, USA)

5.1 Parallel artificial membrane permeability assay (PAMPA). Passive membrane transport properties were measured using a 96-well pre-coated PAMPA plate system with membrane pore size 0.4 µm (Gentest™, Corning; Bedford, MA, USA). Briefly, 1 mM stock solution of each compound was prepared in deionized water, diluted to a final concentration of 400 µM in PBS (Sigma Aldrich; St. Louis, MO), and placed in the plate bottom well (donor well). After 4 h incubation at room temperature, the sample concentration in the donor and acceptor wells were measured using a UV-Vis spectrophotometer (Beckman, DU640) set at the wavelength corresponding to the maximum absorption of each compound. Compound concentration in the donor and acceptor wells were calculated from calibration curves spanning 400-3.125 µM. Samples were tested in triplicates in three separate experiments.

Bi-directional permeability assay with Caco-2 cells. Compounds were tested in a Caco-2 cell bi-directional permeability assay using an established contract research organization (Cyprotex; Watertown, MA, USA). Briefly, Caco-2 cells were seeded in 96-well plates and allowed to grow in culture media for three weeks, feeding at 2-day intervals. To ensure a well-defined Caco-2 cell monolayer prior to initiation of experiments, aliquots of the cell buffers were analyzed by fluorescence to determine the transport of the impermeable dye Lucifer yellow. For apical to basolateral (A→B) and basolateral to apical (B→A) permeability, compounds were added at 10 µM concentration to the apical (A) side and basolateral (B) side, respectively, and the corresponding amount of permeation was determined by measuring compound concentration on the B or A side. The A-side buffer contained 100 µM Lucifer yellow dye, in transport buffer (1.98 g/L glucose in 10 mM HEPES, 1× Hank's balanced salt solution, pH 7.4), and the B-side buffer was transport buffer at pH 7.4. Caco-2 cells were incubated with these buffers for 2 h, and the receiver side buffer was removed for analysis by LC/MS/MS (using bucetin as an analytical internal standard). Data were expressed as permeability (Papp) calculated using the following formula:

$$Papp = \frac{dQ/dt}{C_0 A},$$

where
dQ/dt, rate of permeation
$C_0$, initial concentration of compound
A, area of monolayer (0.11 cm²)
Efflux Ratio ($R_e$) was calculated using the formula:

$$R_e = \frac{Papp(B \to A)}{Papp(A \to B)}.$$

5.2. MTT cell viability assay. 3T3-L1 pre-adipocytes cells (catalog CL-173, American Type Culture Collection; Manassas, VA, USA) were seeded at a density of 2×10³ cells per well in 96-well plates, cultured with standard culture media [DMEM, 4.5 g/L glucose, L-glutamine, sodium pyruvate (Mediatech Inc.; Tewksbury, MA, USA), 10% FBS (Sigma Aldrich; St. Louis, MO, USA), 1% antibiotic-antimycotic solution (Mediatech Inc.; Tewksbury, MA, USA)], and grown for 48 h until >~90% confluent. Cells were treated for 24 h with 0.1-600 µM NNMT inhibitors in cell culture media. A 24 h time point was chosen based on a previous report of using this time period for transfecting or treating 3T3-L1 cells with NNMT anti-sense oligonucleotides or a small molecule NNMT product inhibitor (1-MNA), respectively, for phenotypic measures. MTT (3-(4,5-dimethylthiazol-2-yl)-2,5-diphenyltetrazolium bromide) (ATCC; Manassas, VA, USA) was added to each well and assayed according to the manufacturer's instructions. Absorbance corresponding to the amount of formazan dye produced by treated cells was normalized to that produced by control (untreated) cells to calculate % viable cells in the treated samples.

5.3. Differentiation of 3T3-L1 pre-adipocytes. 3T3-L1 pre-adipocytes cells were cultured with standard culture media (DMEM, 4.5 g/L glucose, L-glutamine, sodium pyruvate, 10% FBS, 1% antibiotic-antimycotic solution) and grown for 48 h before initiating differentiation using the manufacturer's suggested protocol and modified from previous published work. Briefly, standard culture media was supplemented with scheduled addition of adipogenic agents [3-isobutyl-1methyl xanthine (IBMX), Sigma Aldrich; MO, USA), dexamethasone (Sigma Aldrich; MO, USA), insulin (Gibco Life Technologies Inc.; Grand Island, NY, USA)] over 10 days to promote differentiation of 3T3-L1 fibroblasts into adipocytes; a combination of 1 mM IBMX, 1 µM dexamethasone, and 10 µg/ml of insulin in media were added to fully confluent 3T3-L1 fibroblasts for three days (days 0-3) to initiate differentiation. At day 3, the media was replaced with culture media supplemented with insulin (10 µg/ml). After day 6, cells were maintained in culture media until described experiments were begun (days 8-10).

5.4. Quantitative measurement of NNMT reaction product 1-MNA in cultured cells. Cellular 1-MNA concentrations were determined using an ultra-sensitive high-resolution AB Sciex 6500 Q-trap mass spectrometer coupled to an Agilent 1260 ultra-high pressure liquid chromatography (LC/MS/MS) system. Using multiple reaction monitoring (MRM) positive ion mode, the 1-MNA NNMT reaction product was quantified from peak area ratios using AB Sciex Analyst and MultiQuant 2.1 software and the parent precursor and Q3 masses set to m/z 137.1 and 94.1, respectively. Fragment ions at m/z of 92.1 and 77.9 were additionally used for the detection and confirmation of 1-MNA, respectively. Processing of undifferentiated 3T3-L1 pre-adipocytes (day 0) and differentiated adipocytes (day 10) were optimized for recovery and reproducibility of 1-NINA levels across cultured batches of 3T3-L1 cells (~passages 7-8) and the 1-MNA levels were compared between the pre-adipocytes and adipocytes. To determine the effect of NNMT inhibitor on NNMT activity in the pre-adipocytes and differentiated adipocytes (8×10⁴ cells/well seeded prior to beginning differentiation), cells were treated with 30 µM inhibitor for 24 h. Similarly, to compare the relative effects of multiple NNMT inhibitors on NNMT activity in cultured adipocytes, differentiated adipocytes in 6-well plates were treated with 10 µM test compound for 24 h. Following treatment, media was replaced with 80% (v/v) methanol (cooled to −80° C.) containing 500 nmol 6-chloronicotinamide (6-CN) as an internal standard (IS) to extract cellular metabolites. Adherent cells were scrapped, then centrifuged at 4° C. and 13000 g for 15 min, and the resulting supernatants processed using established protocols. Intracellular levels of 1-MNA and as well as the IS were determined from LC/MS/MS peak areas. Data were subsequently normalized to the IS peak area and transformed as % control values for cross-sample comparisons. The above procedure was repeated with inhibitor concentrations spanning 0.3-60 µM to determine the effective concentration (EC50) required to inhibit 50% NNMT activity in cultured adipocytes. Choice of inhibitor concentrations and time period was chosen based on the results from the MTT studies.

5.4. Quantitative measurement of selected metabolites in cultured cells. The relative levels of selected metabolites (NA, SAM, SAH, NAD+) regulated by cellular energy expenditure pathways associated with NNMT were simultaneously detected using LC/MS/MS and MRM ratios. Sample processing was performed as described above. Parent precursor masses of 124.0, 399.3, 385.1, and 665.1 Da and Q3 masses set to m/z 80.0, 250.1, 136.0, and 136.0 were used for the quantitation of NA, SAM, SAH, and NAD+, respectively.

5.5. Selectivity of NNMT inhibitors. Test compounds were screened in biochemical assays for activity against three structurally similar methyltransferases, including catechol-O-methyltransferase (COMT), DNA (cytosine-5)-methyltransferase 1 (DNMT1), and protein arginine methyltransferase 3 (PRMT3). Additional biochemical assays were used to test the ability of compounds to inhibit nicotinamide phosphoribosyl transferase (NAMPT) and NAD+-dependent protein deacetylase sirtuin 1 (SIRT1), two enzymes in the NAD+ biosynthesis/salvage pathway. All assays were performed by Reaction Biology Corporation (RBC; Malvern, PA, USA) and complete assay details are noted below. For each test compound, IC50 values were calculated from dose-response curves established with 10 concentrations of a half-log dilution series. For each assay, established enzyme specific inhibitors were included as positive controls for enzyme function and assay reproducibility. IC50 values were determined by non-linear least-squares fitting of a 4-parameter dose-response curve to collected data points (Graphpad Prism 7.0; La Jolla, CA, USA).

5.5(a). DNMT1 activity assay. A radiometric assay was performed by RBC using 100 µM 5 nM SAH as an inhibitor positive control. The analogues, 1,8-diMQ and 5-amino-1MQ were tested at concentrations from 200 µM-10 nM and 600 µM-10 nM, respectively. Reactions were performed with 0.001 mg/ml DNA substrate Poly(dI-dC), 1 µM radiolabelled S-adenosyl-L-[methyl-3H] methionine (SAM) co-substrate, and recombinant human DNMT1 enzyme. Activity was monitored via quantification of radiolabeled reaction product DNA 5-[methyl-3H]-cytosine.

5.5(b). PRMT3 activity assay. A radiometric assay was performed by RBC using 100 µM-5 nM SAH as an inhibitor positive control. The analogues, 1,8-diMQ and 5-amino-1MQ were tested at concentrations from 200 µM-10 nM and 600 µM-10 nM, respectively. Reactions were performed with 5 µM histone H3 (histone L-arginine) substrate, 1 µM radiolabeled S-adenosyl-L-[methyl-3H] methionine (SAM) co-substrate, and recombinant human PRMT3 enzyme. Activity was monitored via quantification of radiolabeled reaction product histone [methyl-3H]-L-arginine.

5.5(c). COMT activity assay. A radiometric assay was performed by RBC using 1 µM-50 µM tolcapone as an inhibitor positive control. The analogues, 1,8-diMQ and 5-amino-1MQ were tested at concentrations from 200 µM-10 nM and 600 µM-10 nM, respectively. Reactions were performed with 0.5 µM catechol substrate COMT-S01, 1 µM radiolabelled S-adenosyl-L-[methyl-3H] methionine (SAM) co-substrate, and recombinant human COMT enzyme. Activity was monitored via quantification of methylated catechol reaction product (guaiacol [methyl-3H]).

5.5(d). NAMPT activity assay. A fluorometric assay was performed by RBC using 1 µM-50 µM FK866 as an inhibitor positive control. The analogue 5-amino-1MQ was tested at concentrations from 600 µM-30 nM. Reactions were performed with 2 µM nicotinamide and 30 µM phosphoribosyl pyrophosphate (PRPP) in the presence of 1 mM ATP and recombinant human NAMPT enzyme. Activity was monitored using fluorescence detection and quantification of the nicotinamide mononucleotide (NMN) reaction product.

5.5(e). SIRT-1 activity assay. A fluorometric assay was performed by RBC using 100 µM-5 nM suramin sodium as an inhibitor positive control. The analogue 5-amino-1MQ was tested at concentrations from 600 µM-30 nM. Reactions were performed with 50 µM RHKKAc, a fluorogenic peptide substrate from p53 residues 379-382, 500 µM NAD+ co-substrate, and recombinant human SIRT-1 (NAD+-dependent) enzyme. Activity was monitored by the formation of a fluorescent product (coumarin) generated by a two-step coupled reaction that involved deacetylation of substrate by SIRT-1 followed by secondary release of the fluorophore.

5.6. Efficacy of NNMT inhibitor 5-amino-1MQ in diet-induced obese (DIO) mice. 17-week old, male DIO C57Bl/6 mice that have been fed high-fat diet (HFD) for 11 weeks (starting at week 6) were purchased from Jackson Labs (Jackson Laboratory; Bar Harbour, ME, USA). Mice were initially group housed (three/cage) and allowed to acclimate to the colony environment maintained at a constant temperature (21-23° C.) and humidity (40-50%) on a 12-hour light-dark cycle (lights on 0600-1800 h). Upon arrival, mice were continued to be fedHFD (Open Source Diets formula D12451 from Research Diets Inc.; New Brunswick, NJ, USA), containing 45% energy from fat. Water was available ad libitum.

All experiments were carried out in accordance with the Guide for the Care and Use of Laboratory Animals and with approval from the Institutional Animal Care and Use Committee at the University of Texas Medical Branch. Following acclimation for seven days, mice were single-housed and maintained on HFD for 4 additional weeks. Mice were intermittently handled, with body weights and food intake (hopper weights) measured 2-3 times per week. After being fed HFD for a total of 16-weeks (an appropriate rodent model of DIO and comparable to human obesity) and reaching pre-arrival body weights (~38 g), mice were randomized into balanced control and treatment cohorts (n=9/cohort), with similar group average body weight and standard deviation. Mice in the vehicle cohort received three subcutaneous (SC) saline (1 ml/kg) injections/day (~0930, 1330, 1730 h) and mice in the treatment cohort received three SC injections of the NNMT inhibitor 5-amino-1MQ at a dose of 20 mg/kg/injection for a total dose of ~34 mg/kg/day of the parent compound (calculated according to free weight) for 11 days. The dose chosen was based on an initial dose escalation study (ranging from 10 mg/kg/day to a total dose of 150 mg/kg/day) in DIO mice (n=2); a total dose of 60 mg/kg/day was well tolerated with no observable adverse effects. Body weight and food intake were measured every other day. On day 12, mice were subjected to a 4 h fast period, then deeply anesthetized using isoflurane and trunk blood was collected by decapitation. Plasma was separated from every sample and the samples were submitted to Texas A&M Veterinary Medical Diagnostic Laboratory (TVMDL; College Station, TX, USA) for plasma lipid-panel measurements (total cholesterol and triglycerides). Triglycerides values were not included for analysis since the measurements were confounded by sample hemolysis that interfered with the triglyceride reagent in the assay. Epididymal fat pads (epididymal white adipose tissue; EWAT) were excised from every mouse, weighed, and fixed in 10% buffered formalin for further processing.

5.7. Histological analysis. Formalin-fixed EWAT samples were paraffin embedded, sectioned (4 μM), and stained with hematoxylin and eosin (H&E). Images were obtained at 20× magnification using a light microscope (Leica DM LB) and digitally photographed for automated image analysis. Images were analyzed using the "Adiposoft" plug-in software in ImageJ (NIH). Briefly, images were converted to 8-bit images and scald to 0.366 microns per pixel (corresponding to 20× magnification on the Leica microscope). Minimum and maximum diameter parameters were assigned to identify appropriate cells for the automated adipocyte area calculations, and cells along the boundary of the images were excluded from analyses. Three to five images/sample were analyzed, with automated analysis confirmed by visual inspection. Images corresponding to each sample were averaged to obtain the mean adipocyte area (μm2) per sample and combined to calculate group mean values for control (vehicle-treated EWAT samples) and treatment (NNMT inhibitor-treated EWAT samples) cohorts.

5.8. Effect of NNMT inhibitor on adipocyte differentiation quantitated with oil red O staining. 3T3-L1 cells were cultured in 60 mm diameter dishes (8.4×104 cells/dish) and treated with NNMT inhibitor dissolved in culture media with/without adipogenic factors (1 mM IBMX, 1 μM dexamethasone, 10 μg/ml of insulin) during each of the scheduled media changes during the differentiation process (described above). On day 9 post-differentiation, cells were subjected to quantitative oil red O (Thermo Fisher Scientific; Waltham, MA, USA) staining as adapted and modified from published protocols. Briefly, cells were washed twice with PBS, fixed with 10% formalin for 30 min at room temperature, and stained with oil red O working solution (~0.2% oil red O in 99% isopropanol) for 30 min. Cells were then washed five times or with sterile water until unincorporated oil red O stain was completely removed. Images of oil red O staining in control and inhibitor-treated cells were digitally photographed using a light microscope (Olympus BX41; Tokyo, Japan). After image capture, 2-propanol (3.5 mL) was added to each dish for 10 min to dissolve the oil red O stain and absorbance was quantified in a plate reader set at 492 nm wavelength. To ensure the absorbance from oil red O staining was within the linear detection range of the plate reader, a calibration curve was established for oil red O staining in adipocytes using a previously described protocol.

5.9. Statistical analysis. Statistical analysis for two-group comparisons was conducted using unpaired Student's t-test. A one-way analysis of variance (ANOVA) with Dunnett's posthoc test was used to compare multiple groups (different inhibitor treatments or concentration effects in cellular assessments) to controls. Daily NNMT inhibitor effects on body weight measures in DIO mice was analyzed using a repeated measures two-way ANOVA with Sidak's multiple comparison posthoc test. All statistical analyses were performed using Graphpad Prism 7.0 with an experiment-wise error rate of $\alpha=0.05$.

Results 5.10. NNMT inhibitors display high membrane permeability. Compounds spanning ~100-fold IC50 values for NNMT inhibition were selected on the basis of positional substitutions around the N-methylated quinolinium scaffold to obtain an estimate of drug-like oral absorption/bioavailability properties and guide the choice of inhibitors for in vitro and in vivo phenotypic studies. Tables 4 and 5 summarize passive membrane diffusion and active transport membrane permeability, respectively, for select small molecule NNMT inhibitors for which structure activity relationships had been previously developed. 1-MNA, a product inhibitor of NNMT exhibited no passive permeability (Table 4). Similarly, the quinolinium containing parent analogue 1-MQ also lacked passive diffusion properties (Table4), suggesting that the lipophilicity and drug-like permeability properties of analogues within the methylquinolinium series had to be improved via chemical modification. To this end, we synthesized a number of per-methylated quinolinium analogues guided by in silico calculation of partition coefficient (c log P). Addition of hydrophobic methyl group substitutions around the quinolinium scaffold (previously shown to negatively impact NNMT inhibitory activity) only slightly improved membrane permeability via passive transport as indicated by the low, but non-zero, permeability values for 1,8-diMQ and 1,2,4,8-tetraMQ (Table 4). In contrast, positional polar amine substitutions around the quinolinium core not only improved NNMT inhibition as noted previously, but also enabled favorable passive and active transport across membranes (Tables 4 and 5). Specifically, 5-amino-1MQ and 7-amino-1MQ exhibited high passive and active transport across membrane, with no detectable efflux observed in the Caco-2 cell assay. In contrast, the 2,3-diamino substitution in the 1MQ scaffold (2,3-diamino-1MQ) displayed high passive permeability (Table 4), but moderate bi-directional active transport with moderate efflux ratio (Table 5). Consistent with the PAMPA measurements, the 1,8-diMQ analogue exhibited very low bi-directional transport in the Caco-2 cell assay (Table 5).

we measured the expression levels of NNMT and used LC/MS/MS to assess the levels of NNMT reaction product 1-MNA in fully differentiated adipocytes (day 9-10 post-differentiation) and undifferentiated pre-adipocytes (day 0). NNMT protein expression was found to be ~37-fold higher in the adipocytes (day 9) vs pre-adipocyte ($P<0.0001$).

TABLE 4

NNMT inhibitor permeability from passive transport across membranes as measured using PAMPA

| Name | $IC_{50}$ (μM)[a] | Flux (cm/s) | Permeability Classification[b] |
|---|---|---|---|
| Quinoline (highly permeable)[c] | ND | 33.9E−06 | High permeability |
| 1-methylnicotinamide (1-MNA) | 9.0 | 0 | No permeability |
| 1-methylquinolinium (1-MQ) | 12.1 | 0 | No permeability |
| 1,8-diMQ | 1.8 | 8.63702E−07 | Low permeability |
| 1,2,4,8-tetraMQ | 109.2 | 6.98184E−07 | Low permeability |
| 5-amino-1MQ | 1.2 | 3.01472E−06 | High permeability |
| 3-amino-6-fluoro-1MQ | 1.2 | 1.07832E−06 | Moderate permeability |
| 7-amino-1MQ | 2.6 | 2.05476E−06 | High permeability |
| 2,3-diamine-1MQ | 2.8 | 3.89795E−06 | High permeability |

[a]$IC_{50}$ values from our published SAR study[17]
[b]BCS, Biopharmaceutics Classification System
[c]High membrane-permeable comparator compound[51]
ND: Not determined; Quinoline is an NNMT substrate[25]

TABLE 5

Active transport across cell membranes and drug efflux ratios for NNMT inhibitors determined using Caco-2 assay

| Name | Mean A→B Papp $10^{-5}$ cm/s | Mean B→A Papp $10^{-5}$ cm/s | Efflux Ratio ($R_e$) | Classification |
|---|---|---|---|---|
| Ranitidine[a] | 0.192 | 1.44 | 11.9 | Low permeability (control) |
| Talinolol[a] | 23.5 | 15.7 | 0.673 | High permeability (control) |
| Warfarin[a] | 0.0701 | 5.01 | 73.2 | High efflux (control) |
| 1,8-diMQ | BLQ | 1.78 | NC | Low permeability |
| 5-amino-1MQ | 34.2 | 45.2 | 1.33 | High permeability (no efflux) |
| 7-amino-1MQ | 26.0 | 39.6 | 1.52 | High permeability (no efflux) |
| 2,3-diamine-1MQ | 5.27 | 21.2 | 4.03 | Moderate permeability (moderate efflux) |

[a]Standard controls used in the assay based on permeability classifications
BLQ: No peak detected in receiver side sample for A→B transport
NC: not calculable 5.11. Effects of NNMT inhibitors on 3T3-L1 cell viability. The cytotoxic effects of three membrane-permeable NNMT inhibitors, 5-amino-1MQ, 7-amino-1MQ, and 2,3-diamino-1MQ were evaluated in 3T3-L1 pre-adipocytes. Treatment of cells with 10 μM 5-amino-1MQ or 7-amino-1MQ and 300 μM 2,3-diamino-1MQ for a 24 h period did not impact cell viability (FIG. 1). 5-amino-1MQ and 7-amino-1MQ produced modest cytotoxicity relative to untreated cells ($P<0.01$, treated vs. control untreated cells) at concentrations ranging from 100-300 μM. All three compounds displayed ~40% cytotoxicity at the highest concentration tested ($P<0.001$, 600 μM-treated cells vs. control untreated cells).

5.12. Differentiated 3T3-L1 adipocytes provide a relevant cell-based system to validate NNMT inhibitor mechanism-of-action. To determine if differentiated 3T3-L1 adipocytes could be utilized as a cell-based system for mechanism-of-action and phenotypic characterization of NNMT inhibitors, Similarly, 1-MNA levels normalized to total cellular protein were ~7.5-fold higher in adipocytes compared to pre-adipocytes ($P<0.05$, pre-adipocytes vs. adipocytes), suggesting relatively higher activity of the NNMT enzyme in the fully differentiated adipocytes. NNMT inhibition using 5-amino-1MQ (30 μM concentration) in both the pre-adipocytes ($P<0.01$, treated pre-adipocytes vs. untreated controls) and the adipocytes ($P<0.05$, treated adipocytes vs. untreated controls) resulted in significant reduction in the intracellular levels of 1-MNA.

Figure 6:
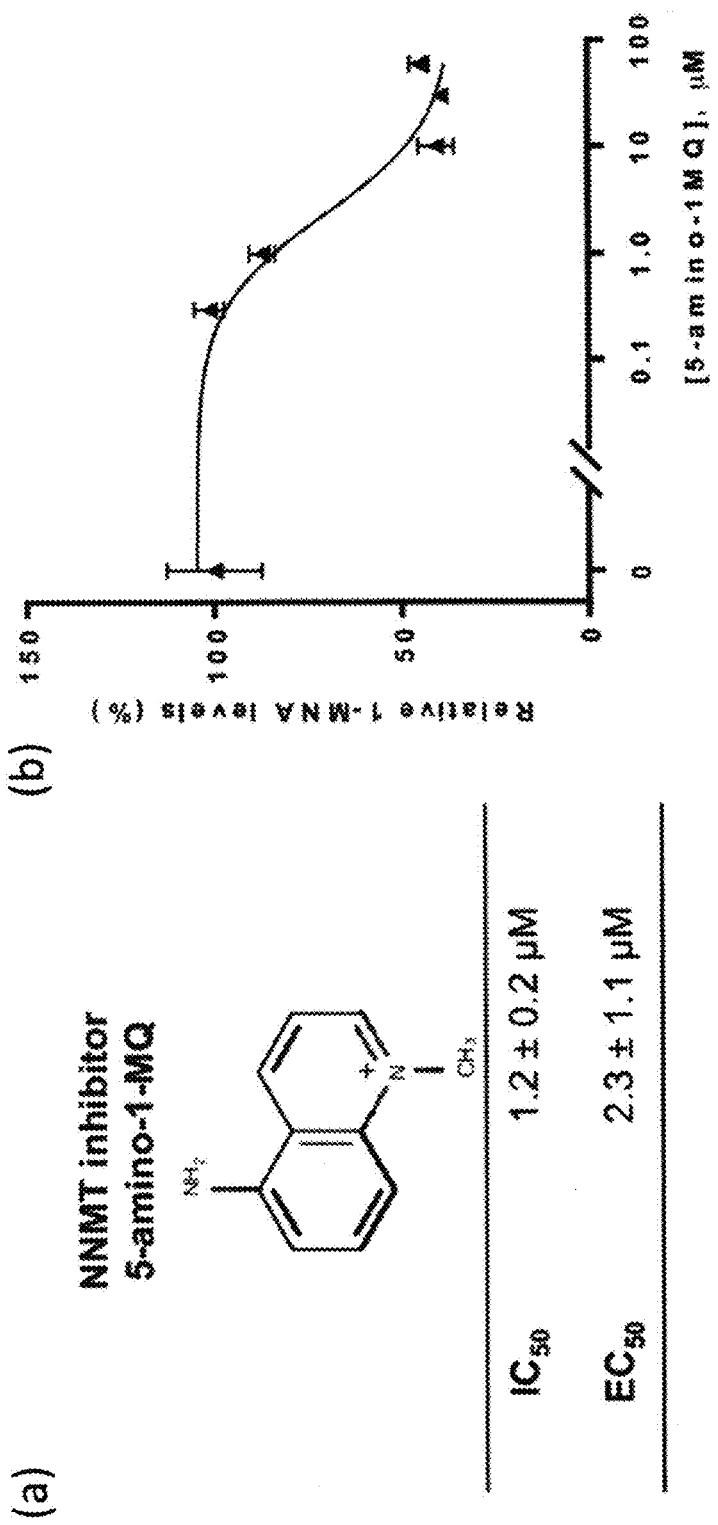
FIG. 6. (a). Dose-response curve showing intracellular 1-MNA levels in adipocytes following treatment with varied 5-amino-1MQ concentrations (b). Data points represent average 1-MNA levels normalized to an internal standard and transformed to % control values±SD (n=2 replicates per data point). The goodness-of-fit R2 between fitted curves and data was 0.94. #, P<0.05 vs. control pre-adipocytes; *, P<0.05; , P<0.01; *, P<0.001 vs. control adipocytes; ^, P<0.01, vs. 5-amino-1MQ (10 µM)-treated adipocytes analyzed by Student's t-test or one-way ANOVA with Dunnett's posthoc where appropriate.

5.13. NNMT inhibitors decrease production of 1-MNA in differentiated adipocytes. The relative effectiveness of NNMT inhibitors to lower 1-INA levels in the differentiated adipocytes were compared at a single concentration of 10 μM (concentration well below the cytotoxic concentration range for NNMT inhibitors). Treatment of adipocytes with membrane-permeable NNMT inhibitors for 24 h resulted in a significant reduction in cellular 1-MNA levels, relative to the levels of 1-MNA in untreated control adipocytes (F(5, 6)=42.64, P<0.0001). Dunnett's posthoc tests revealed that all membrane-permeable NNMT inhibitors tested significantly decreased 1-MNA levels in the adipocytes relative to control (5-amino-1MQ, P<0.001; 3-amino-6-fluoro-1MQ, P<0.01; and 2,3-diamino-1MQ, P<0.05 vs. control untreated adipocytes, respectively). In contrast, the poorly membrane-permeable NNMT inhibitor 1,2,4,8-tetraMQ did not significantly decrease intracellular 1-MNA levels compared to untreated controls (P>0.05, n.s.). 5-amino-1MQ, an analogue from our initial series of NNMT inhibitors with low $IC_{50}$ value ($IC_{50}=\sim1$ µM), and high cell membrane permeability (Table 5), produced the greatest reduction of intracellular 1-MNA levels at a concentration of 10 µM among tested inhibitors. Based on these results, we monitored changes in intracellular 1-MNA in response to 24 h treatment with varied 5-amino-1MQ concentrations. 5-amino-1MQ showed concentration-dependent inhibition of NNMT in fully differentiated adipocytes that could be fit to a 3-parameter sigmoidal dose-response curve with a calculated $EC_{50}=2.3+/-1.1$ µM (FIGS. 6A-B; goodness-of-fit $R^2=0.94$). At inhibitor concentrations ranging from 10-60 µM, the relative intracellular 1-MNA levels stabilized at ~40% the level observed for untreated adipocytes; concentrations greater than 60 µM were not tested due to known cytotoxic effects in 3T3-L1 cells.

Figure 1A:
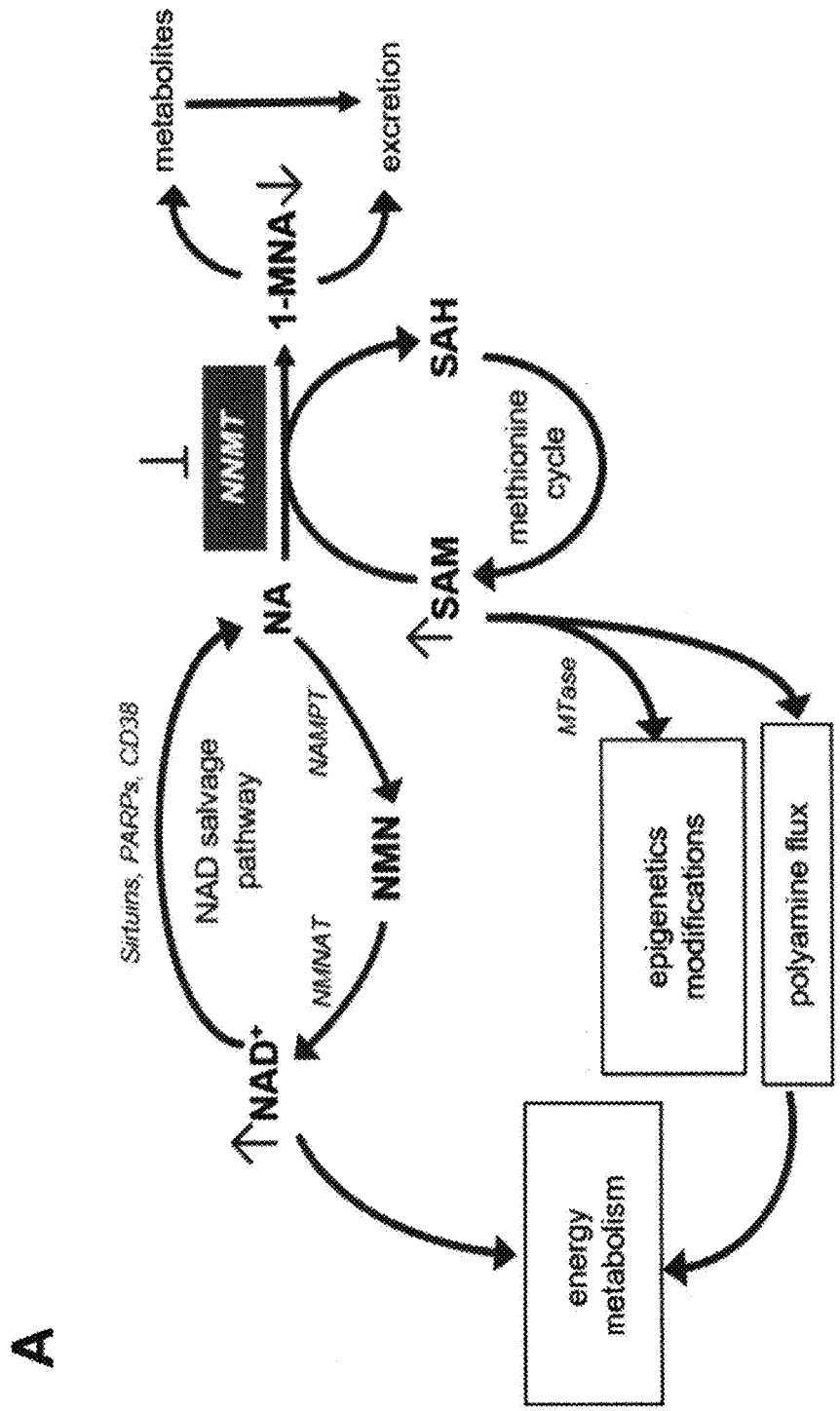
FIG. 1A. Schematic illustration of pathways regulated by NNMT, including the NAD+ biosynthesis salvage pathway starting from NA as a precursor that feeds into energy metabolism, methionine cycle that regulates intracellular SAM concentrations and thus cellular epigenetic modifications and polyamine flux, and clearance of NA by conversion to 1-MNA and excretory products. Pathway enzyme abbreviations include NMNAT (nicotinamide mononucleotide adenylyltransferase), NAMPT (nicotinamide phosphoribosyltransferase), MTase (SAM-dependent methyltransferases), PARPs (poly-ADP-ribose polymerases), and CD38 (cluster of differentiation 38/cyclic ADP ribose hydrolase).
Figure 1B:
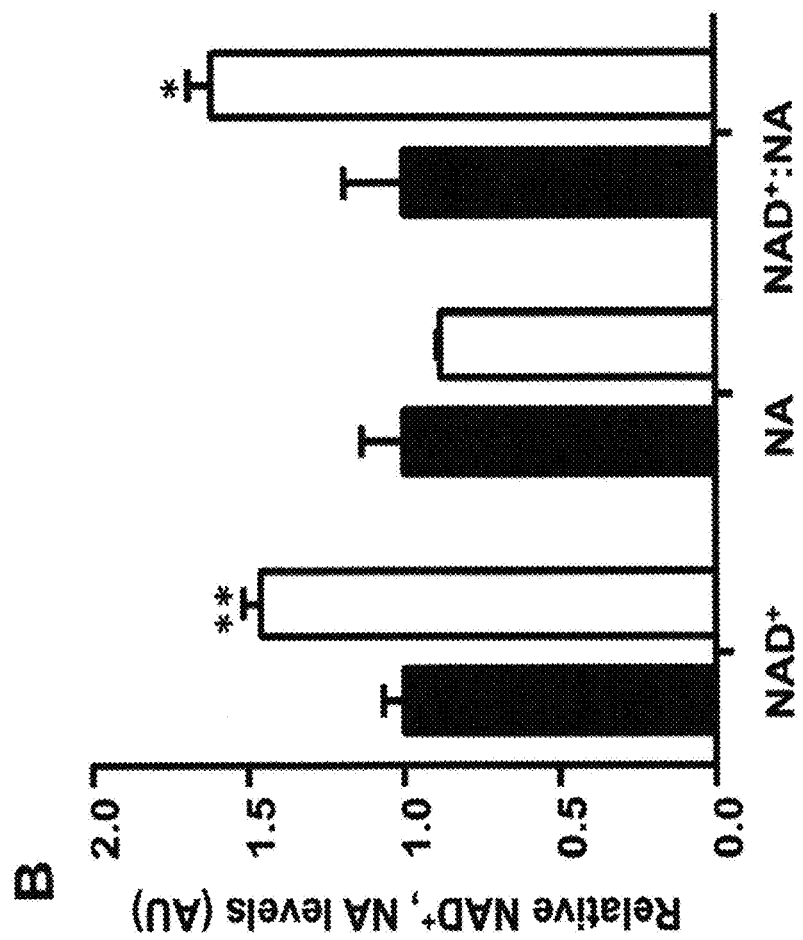
FIG. 1B. Effects of the NNMT inhibitor 5-amino-1MQ on intracellular levels of (B) NAD+, NA, NAD+:NA ratio in differentiated adipocytes (3T3 cells) treated with the inhibitor (30 µM) for 24 h. Data represent mean metabolite levels measured by LC/MS/MS in 5-amino-1MQ-treated adipocytes (open bar) normalized to control untreated adipocyte (closed bar) levels in biological duplicates (±SD). *, P<0.05; **, P<0.01 vs. control untreated adipocytes analyzed by unpaired Student's t-test.
Figure 1C:
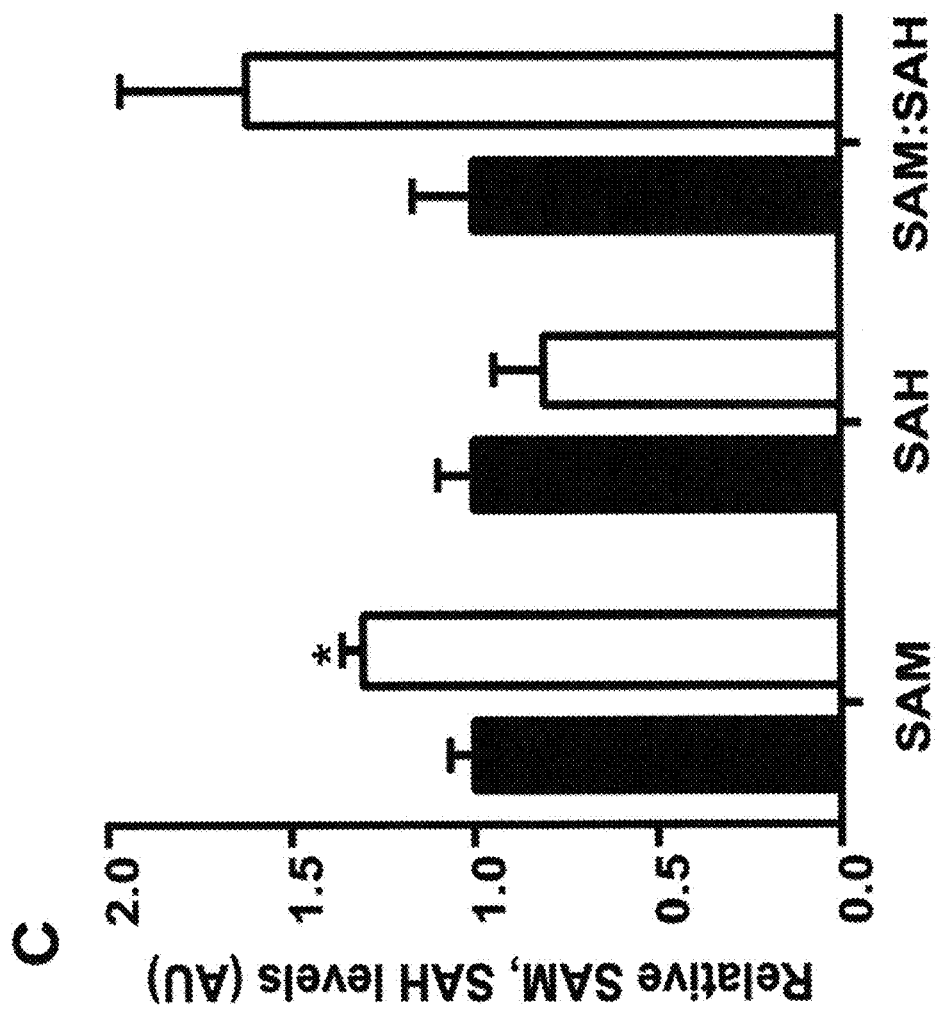
FIG. 1C. Effects of the NNMT inhibitor 5-amino-1MQ on intracellular levels of SAM, SAH, SAM:SAH ratio in differentiated adipocytes (3T3 cells) treated with the inhibitor (30 µM) for 24 h. Data represent mean metabolite levels measured by LC/MS/MS in 5-amino-1MQ-treated adipocytes (open bar) normalized to control untreated adipocyte (closed bar) levels in biological duplicates (±SD). *, P<0.05; **, P<0.01 vs. control untreated adipocytes analyzed by unpaired Student's t-test.
Figure 7:
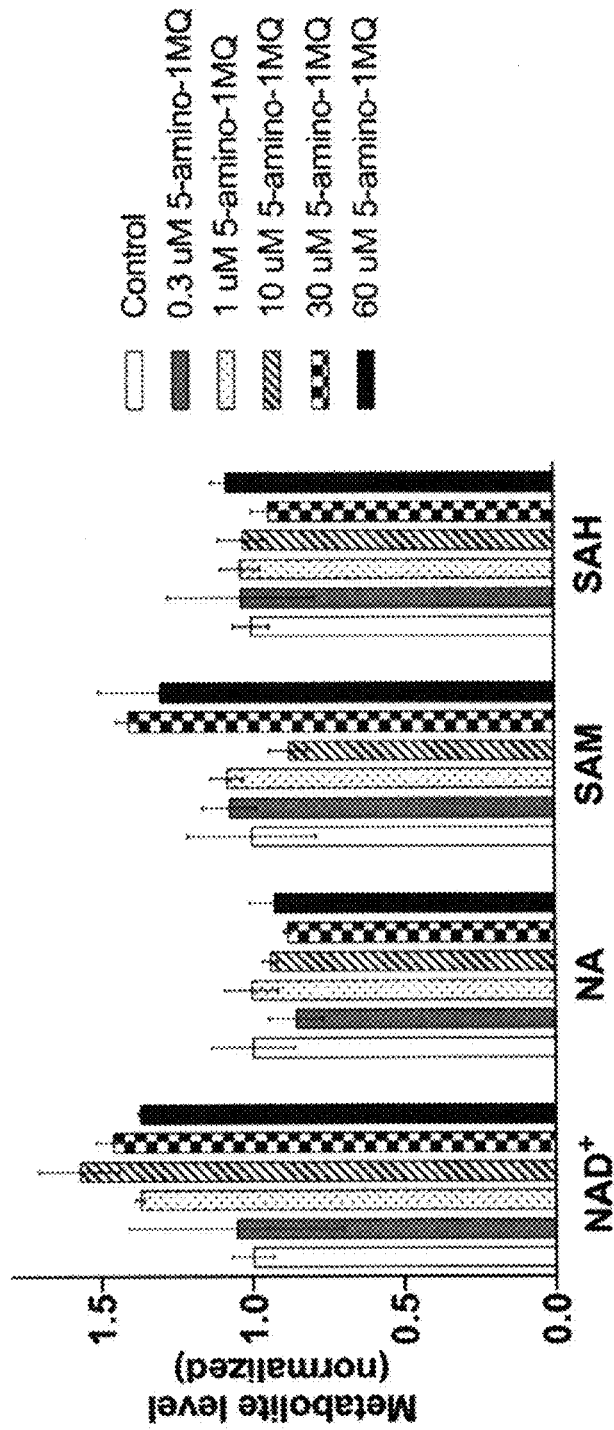
FIG. 7. Data represent mean metabolite levels measured by LC/MS/MS in 5-amino-1MQ-treated adipocytes (open bar) normalized to control untreated adipocyte (closed bar) levels in biological duplicates (±SD). *, P<0.05 vs. control untreated adipocytes determined by one-way ANOVA analyses followed by Dunnett's postests comparisons.

5.14. NNMT inhibition increases intracellular concentrations of NAD+ and SAM in differentiated adipocytes. FIG. 1A outlines the major elements of the mammalian NAD+ salvage pathway using NA as the starting substrate. Since the NNMT inhibitor 5-amino-1MQ significantly reduced intracellular 1-MNA concentrations, we hypothesized that NNMT inhibition in adipocytes would increase intracellular concentrations of the co-substrates NA and SAM and shunt more NA into the NAD+ salvage cycle. A one-way ANOVA revealed an almost significant main effect of NNMT inhibitor treatment on intracellular NAD+ levels (F(5,6)=4.131, P=0.0568) (FIG. 7); treatment of the adipocytes with the NNMT inhibitor 5-amino-1MQ resulted in a concentration-dependent increase in the NAD+ levels with concentrations in the range of 1-60 µM resulting in ~1.2-1.6-fold increase in NAD+ levels relative to control adipocytes. Dunnett's posttests revealed a significant increase in NAD+ levels at the 10 µM inhibitor concentration (P<0.05 vs. control; FIG. 7). Similarly, a one-way ANOVA revealed a significant main effect of NNMT inhibition on intracellular SAM levels (F(5.5)=7.35, P=0.0236) in the adipocytes (FIG. 7). Dunnett's posttests revealed a significant increase in the intracellular SAM levels at the higher inhibitor concentration relative to control adipocytes (30 µM, P<0.05; 60 µM, P=0.06). However, no statistically significant main effect of NNMT inhibitor treatment were observed for the intracellular levels of NA (F(5,6)=1.031, P>0.05) and (F(5,6)=0.334, P>0.05) SAH (FIG. 3B).

5.15. NNMT inhibitors are selective and do not impact related methyltransferases or enzymes in the NAD+ salvage pathway. The selectivity of NNMT inhibitors was confirmed by testing against a panel of structurally similar methyltransferases and two enzymes in the NAD+ salvage pathway (NAMPT and SIRT1; FIGS. 1A and 7). Concentrations of 1,8-diMQ and 5-amino-1MQ ranging from 10 nM to 200 or 600 µM, respectively, did not inhibit DNMT1 or PRMT3. Sigmoidal dose-response curves and reliable estimates of $IC_{50}$ values based on non-linear least-squares fitting to the available data could not be obtained since no significant inhibition of DNMT1 and PRMT3 was observed at the tested NNMT inhibitor concentrations (Table 6). Additionally, 1,8-diMQ and 5-amino-1MQ showed little inhibition of COMT at maximal tested concentrations of 200 µM (20% inhibition) and 600 µM (10% inhibition), respectively, although no clear trend of concentration-dependent inhibition was observed. As was noted for DNMT1 and PRMT3, sigmoidal dose-response curves and reliable estimates of $IC_{50}$ values could not be obtained since no significant inhibition was observed at the tested NNMT inhibitor concentrations.

5-amino-1MQ did not inhibit NAMPT up to a tested concentration of 100 µM; reliable data could not be obtained at 5-amino-1MQ concentrations above 100 µM due to inference with the NAMPT assay readout signal (Table 6). However, when the assay was repeated with 5-amino-6-fluoro-1MQ, an analogue of 5-amino-1MQ that did not interfere with the NAMPT assay, no inhibition of NAMPT was observed with analogue concentrations between 30 and 600 µM (data not shown).

5-amino-1MQ did not inhibit SIRT1 concentrations ranging from 10 nM-300 µM, and minor reduction in SIRT1 activity was observed with 600 µM 5-amino-1MQ. However, sigmoidal dose-response curves and reliable estimates (i.e., $R^2>0.8$) of $IC_{50}$ values could not be obtained since no significant inhibition was observed with the tested concentrations of 5-amino-1MQ. Taken together, these results suggest high selectivity of the small molecule 5-amino-1MQ analogue at pharmacologically relevant concentrations to NNMT-inhibition.

TABLE 3

Activity for NNMT inhibitors against related methyltransferases and enzymes in the NAD+ salvage pathway

| | $IC_{50}$ (µM) | | |
| --- | --- | --- | --- |
| Enzyme | Positive control | 1,8-diMQ | 5-amino-1MQ |
| DNA (cytosine-5)-methyltransferase 1 | 0.28 ± 0.03 (SAH) | NI | NI |
| Protein arginine methyltransferase 3 | 6.6 ± 1.2 (SAH) | NC | NC |
| Catechol-O-methyltransferase | 0.0009 ± 0.0001 (Talcapone) | NC | NC |

TABLE 3-continued

Activity for NNMT inhibitors against related methyltransferases and enzymes in the NAD+ salvage pathway

| Enzyme | IC$_{50}$(μM) | | |
|---|---|---|---|
| | Positive control | 1,8-diMQ | 5-amino-1MQ |
| Nicotinamide phosphoribosyl transferase | 0.0038 ± 0.0001 (FK866) | ND | >100[a] |
| NAD$^+$-dependent protein deacetylase sirtuin 1 | 4.3 ± 0.6 (Suramin) | ND | NC |

NI: no inhibition
NC: not calculable
ND: not determined
[a]concentrations above 100 μM could not be tested due to inference in the assay readout signal 5.16. NNMT inhibitor caused weight loss and reduced adipose tissue mass in DIO mice. Since in vitro studies showed 5-amino-1MQ to have high cell permeability, enzyme selectivity, and cell culture efficacy, a sub-chronic (11-day) proof-of-concept in vivo study was conducted to test the effect of NNMT inhibition on obesity in HFD fed mice. Three times daily systemic (SC) treatment of DIO mice with 20 mg/kg of 5-amino-1MQ produced a progressive loss of body weight over the treatment period compared to controls (FIG. 8A). A repeated-measures two-way ANOVA revealed a significant main effect of the factors treatment ($F(1,16)=12.47$, $P=0.0028$), time (days) ($F(5,80)=4.437$, $P=0.0012$), and a significant treatment×time interaction ($F(5,80)=10.89$, $P<0.0001$).

Sidak's multiple comparison posttests revealed significant differences in body weight between control and treated DIO mice on days 6 ($P<0.01$), 9 ($P<0.0001$), and 10 ($P<0.0001$) (FIG. 8A). At the end of the 11-day treatment period, control DIO mice showed a cumulative weight gain of 0.6±0.4 g (~1.4% weight gain from baseline measures), while DIO mice treated with the NNMT inhibitor showed a weight loss of 2.0±0.6 g (~5.1% weight loss from baseline measures) (FIG. 8A). Food intake remained the same between the groups suggesting the weight loss effect is primarily related to altered metabolism ($F(1,16)=1.101$, $P>0.05$; FIG. 8B); total cumulative food intake in control and treated DIO mice was 28.1±1.2 g and 26.2±1.4 g, respectively (FIG. 8B, inset). Additionally, treatment of DIO mice with the NNMT inhibitor resulted in a substantial ~35% decrease ($P<0.001$) in the mass (FIG. 8C) and size (FIG. 8D) of the EWAT compared with the control DIO mice. Consistent with these results, histological analysis of the EWAT from treated DIO mice had >30% decrease in adipocyte size ($P<0.05$; FIGS. 8E and 8F) and >40% decrease in adipocyte volume (data not shown) compared to control DIO mice. Plasma lipid-profile measurements showed that the total cholesterol levels were ~30% lower in treated DIO mice relative to control DIO mice ($P<0.05$; FIG. 8G). Total cholesterol levels at the end of our study in the control DIO mice were comparable to cholesterol levels reported by the vendor for age-matched DIO mice. In contrast, cholesterol levels in the NNMT inhibitor-treated DIO mice were similar to cholesterol levels reported by the vendor for age-matched normal chow-fed C57B1/6 mice (www.jax.org/jax-mice-and-services/find-and-order-jax-mice/most-popular-jax-mice-strains/dio-b6).

Figure 9A:
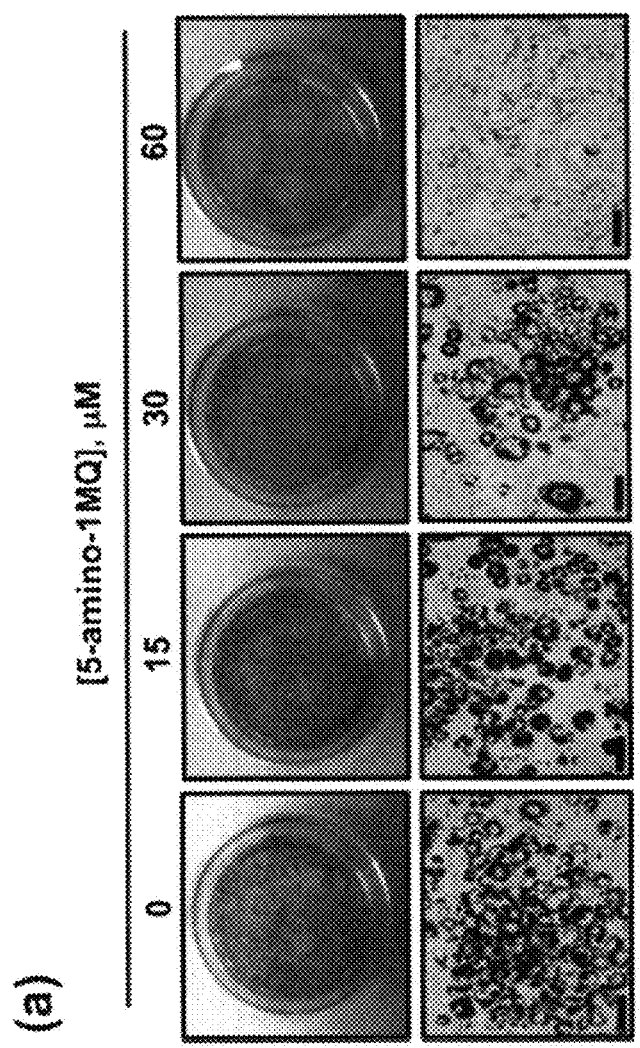
Figure 10:
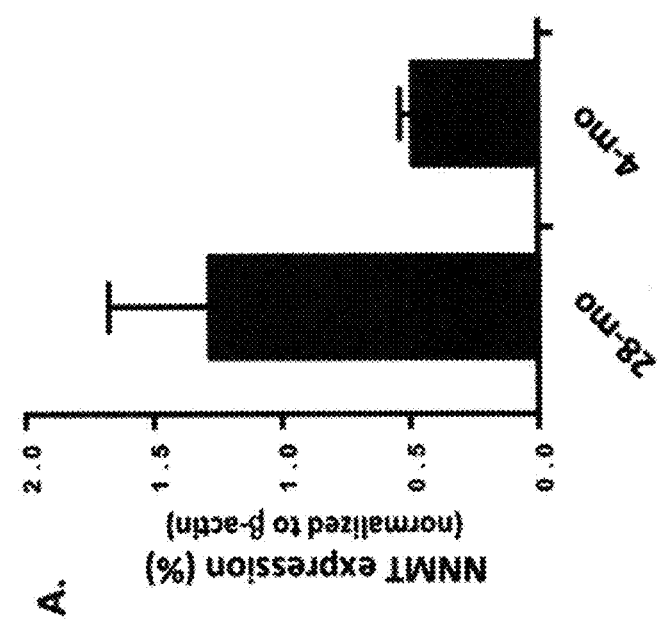
FIG. 10. NNMT protein is highly expressed in aged (28 mo) tibialis anterior (TA) skeletal muscle tissue vs. young (4 mo) TA muscle tissue.
Figure 11A:
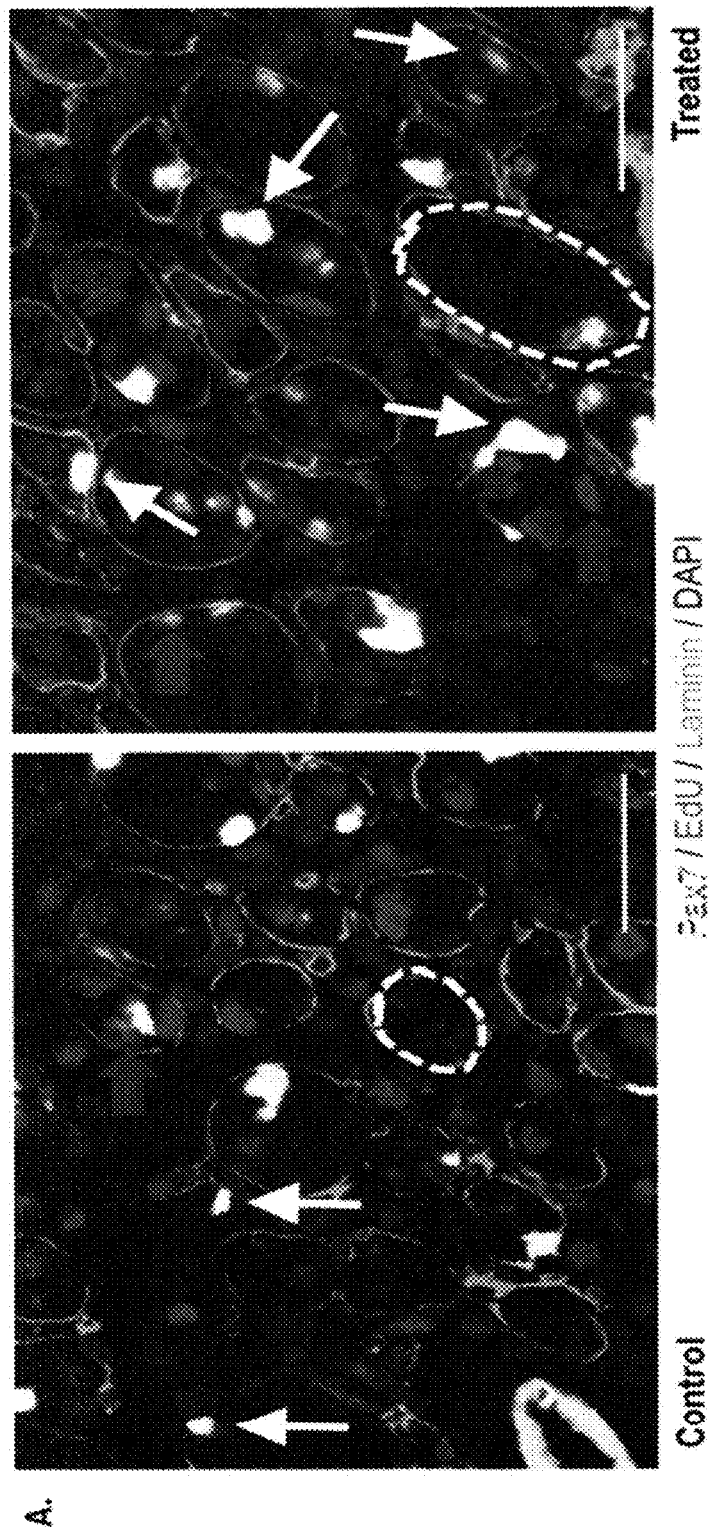
Figure 12:
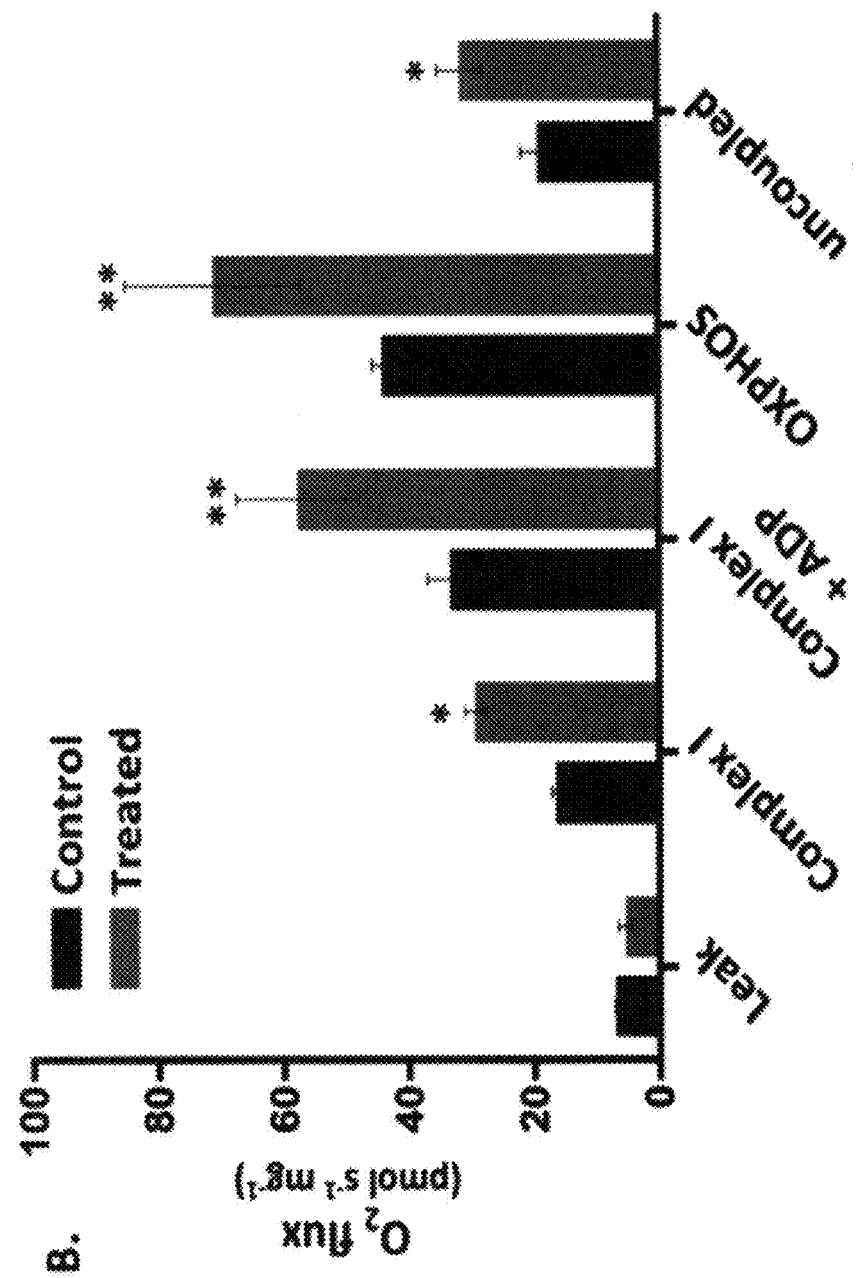
FIG. 12. Treatment with NNMT inhibitor increased mitochondrial respiration capacity and oxidative phosphorylation in the quadriceps skeletal muscle of aged mice (>24 mo old).

5.17. NNMT inhibition suppresses lipogenesis in 3T3-L1 cells. In order to determine the effect of NNMT inhibition on adipocyte differentiation and lipogenesis, lipid accumulation was determined in adipocytes following treatment of 3T3-L1 cells with the NNMT inhibitor in media containing adipogenic factors. Treatment with 5-amino-1MQ produced concentration-dependent inhibition of lipid accumulation in differentiating pre-adipocytes ($F(3,19)=39.26$, $P<0.0001$; FIGS. 9A and 9B). Concentrations of 30 μM and 60 μM 5-amino-1MQ reduced lipogenesis by 50% and 70%, respectively, compared to control untreated adipocytes ($P=0.0001$; FIG. 9B). 3T3-L1 cell viability was only slightly reduced at the highest tested concentration of 5-amino-1MQ compared to untreated cell viability ($P<0.05$; FIG. 9C).

We claim:

1. A cation of Formula I, wherein:

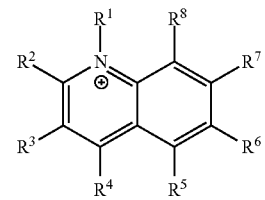

Formula I $R^1$ is $C_{1-4}$ alkyl;
$R^2$ is independently selected from the group consisting of: H, halogen-substituted $C_{1-4}$ alkyl, $NR^9R^{10}$, and CN;
$R^3$ is independently selected from the group consisting of: H, halogen-substituted $C_{1-4}$ alkyl, $NR^9R^{10}$, and CN;
$R^4$ and $R^5$ are independently selected from the group consisting of: H, $C_{1-4}$ alkyl, halogen-substituted $C_{1-4}$ alkyl, $NR^9R^{10}$, and CN;
$R^6$ is H or halogen;
$R^7$ is H, methyl, or $NR^{11}R^{12}$; and
$R^8$ is H, $C_{1-4}$ alkyl, halogen-substituted $C_{1-4}$ alkyl;
$R^9$, $R^{10}$, $R^{11}$, and $R^{12}$ are independently selected from H and $C_{1-4}$ alkyl, wherein $R^9$ and $R^{10}$, are independently selected from $C_{1-4}$ alkyl when $R^4$ is $NR^9R^{10}$;
wherein the cation has at least two non-hydrogen substituents at positions $R^2$-$R^8$;
and wherein at least one of $R^2$, $R^3$, $R^5$, and $R^7$ is $NH_2$.

2. The cation of claim 1, wherein $R^1$ is methyl or ethyl.
3. The cation of claim 1, wherein $R^1$ is methyl.
4. The cation of claim 1, wherein at least one of $R^2$ and $R^3$ is $NH_2$.
5. The cation of claim 1, wherein $R^5$ is $NH_2$.
6. The cation of claim 1, wherein $R^2$, $R^3$, and $R^4$ are hydrogen.
7. The cation of claim 1, wherein $R^6$ is halogen.
8. The cation of claim 1, wherein $R^6$ is F.
9. The cation of claim 1, wherein $R^7$ is $NH_2$.
10. The cation of claim 1, wherein $R^8$ is methyl or $CF_3$.

11. The cation of claim 10, wherein $R^8$ is methyl.

12. The cation of claim 1, wherein said cation is chosen from:

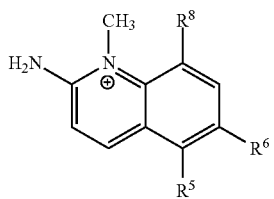
1c'

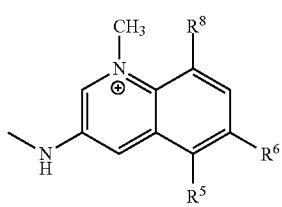
1f'

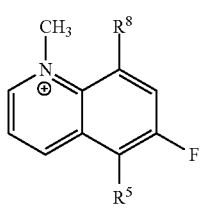
1m'

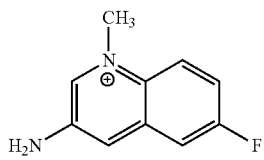
2j

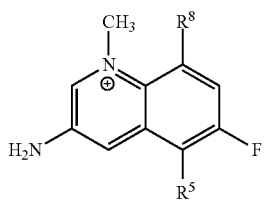
2j'

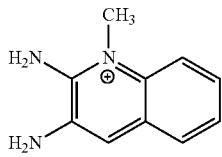
2m

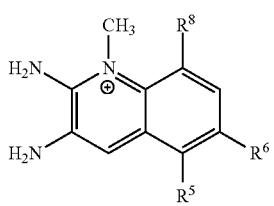
2m'

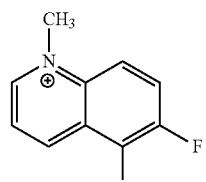
2aa

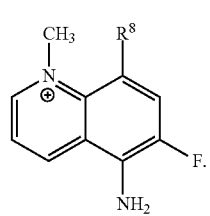
2aa'

13. A method of providing muscular therapy to a subject comprising administration of a cation, said cation chosen from:

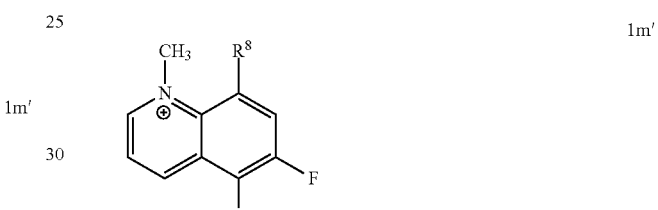
1m'

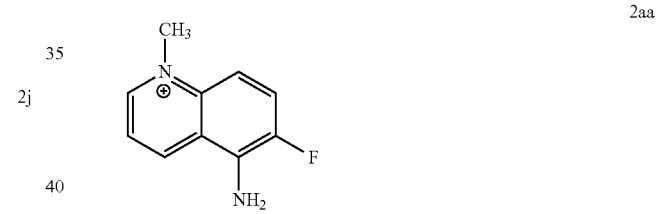
2aa

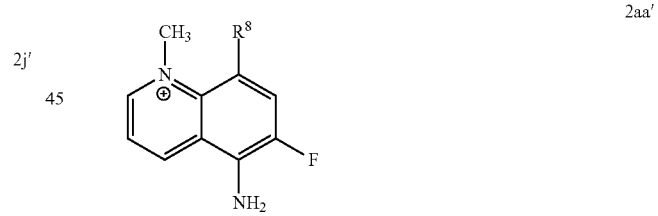
2aa' wherein $R^5$ is H or $NH_2$ and $R^8$ is H or methyl, and wherein the cation includes a non-hydrogen substituent at either of positions $R^5$ and $R^8$.

14. The method of claim 13, wherein said cation is:

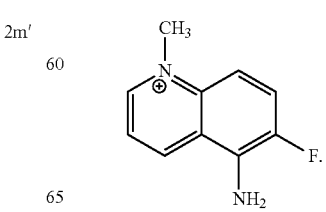
2aa

15. A method of providing muscular therapy to a subject comprising administering a cation of Formula I, wherein:

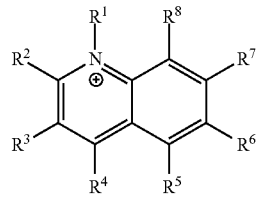

Formula I

R¹ is $C_{1-4}$ alkyl;

R², R³, R⁴, and R⁵ are independently selected from the group consisting of: H, $C_{1-4}$ alkyl, halogen-substituted $C_{1-4}$ alkyl, $NR^9R^{10}$, and CN;

R⁶ is H or halogen;

R⁷ is H, methyl, or $NR^{11}R^{12}$; and

R⁸ is H, $C_{1-4}$ alkyl, halogen-substituted $C_{1-4}$ alkyl;

R⁹, R¹⁰, R¹¹, and R¹² are independently selected from H and $C_{1-4}$ alkyl;

wherein the cation has at least two non-hydrogen substituents at positions R²-R⁸, and wherein at least one of the non-hydrogen substituents at positions R²-R⁸ is NH₂.

16. The method of claim 15, wherein said cation is chosen from:

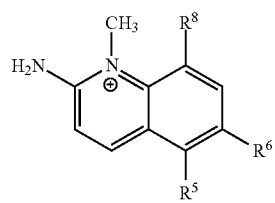

1c'

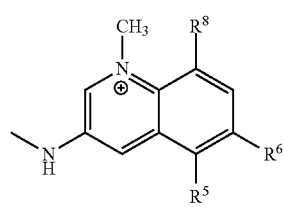

1f'

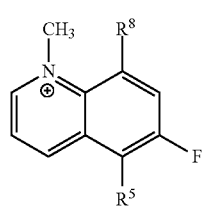

1m'

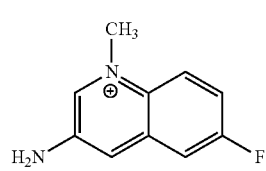

2j

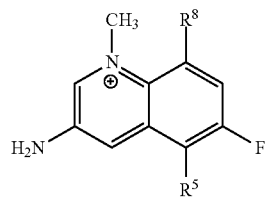

2j'

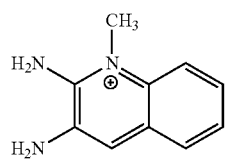

2m

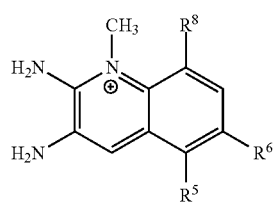

2m'

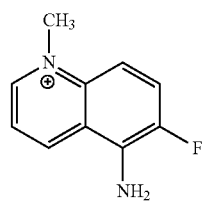

2aa

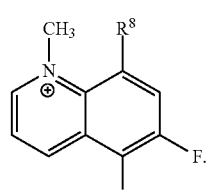

2aa'

17. The cation of claim 1, wherein said cation is accompanied by a counter ion.

18. The cation of claim 17, wherein said counter ion is chosen from sulfonate, halide, acetate, sulfate, bisulfate, nitrate, oxalate, valerate, oleate, palmitate, stearate, laurate, borate; benzoate, lactate, phosphate, citrate, maleate, fumarate, succinate, tartrate, glucoheptonate, and lactobionate.

19. The cation of claim 18, wherein said counter ion is chloride, maleate, besylate or sulfate.

20. The cation of claim 12, wherein said cation is accompanied by a counter ion chosen from chloride, maleate, besylate and sulfate.

21. A method of treating obesity or related chronic metabolic conditions by administering a therapeutically effective amount of one or more cations of Formula I, wherein Formula I is represented as:

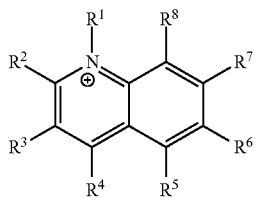

Formula I wherein:
R¹ is $C_{1-4}$ alkyl;
$R^2$, $R^3$, $R^4$, and $R^5$ are independently selected from the group consisting of: H, $C_{1-4}$ alkyl, halogen-substituted $C_{1-4}$ alkyl, $NR^9R^{10}$, and CN;
$R^6$ is H or halogen;
$R^7$ is H, methyl, or $NR^{11}R^{12}$; and
$R^8$ is H, $C_{1-4}$ alkyl, halogen-substituted $C_{1-4}$ alkyl;
$R^9$, $R^{10}$, $R^{11}$, and $R^{12}$ are independently selected from H and $C_{1-4}$ alkyl;
wherein the cation has at least two non-hydrogen substituents at positions $R^2$-$R^8$;
and wherein at least one of the non-hydrogen substituents at positions $R^2$-$R^8$ is $NH_2$.

22. The method of claim 21, wherein said obesity or related chronic metabolic condition is chosen from metabolic syndrome, pre-diabetes, type-2 diabetes, and obesity-linked disease.

23. The method of claim 22, wherein said obesity-linked disease is non-alcoholic fatty liver disease, non-alcoholic steatohepatitis, or CVD.

24. A method of treating a disease, said method comprising administering a therapeutically effective amount of a cation of the following formula:

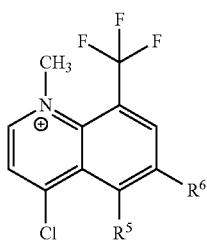

21' wherein:
$R^5$ is selected from the group consisting of: H, $C_{1-4}$ alkyl, halogen-substituted $C_{1-4}$ alkyl, $NR^9R^{10}$, and CN;
$R^6$ is H or halogen; and
$R^9$, and $R^{10}$ are independently selected from H and $C_{1-4}$ alkyl;
wherein said disease is chosen from obesity or related chronic metabolic conditions.

25. The method of claim 24, wherein said obesity or related chronic metabolic condition is chosen from metabolic syndrome, pre-diabetes, type-2 diabetes, and obesity-linked disease.

26. The method of claim 25, wherein said obesity-linked disease is non-alcoholic fatty liver disease, non-alcoholic steatohepatitis, or CVD.

27. A cation of the following formula:

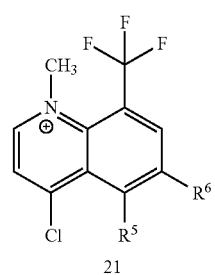

21'

21 wherein:
$R^5$ is selected from the group consisting of: H, $C_{1-4}$ alkyl, halogen-substituted $C_{1-4}$ alkyl, $NR^9R^{10}$, and CN;
$R^6$ is H or halogen; and
$R^9$, and $R^{10}$ are independently selected from H and $C_{1-4}$ alkyl.

28. The cation of claim 27, wherein said cation is accompanied by a counter ion.

29. The cation of claim 28, wherein said counter ion is chosen from sulfonate, halide, acetate, sulfate, bisulfate, nitrate, oxalate, valerate, oleate, palmitate, stearate, laurate, borate; benzoate, lactate, phosphate, citrate, maleate, fumarate, succinate, tartrate, glucoheptonate, and lactobionate.

30. The cation of claim 28, wherein said counter ion is chloride, maleate, besylate or sulfate.

\* \* \* \* \*